US011017881B2

(12) United States Patent
Bermeister et al.

(10) Patent No.: US 11,017,881 B2
(45) Date of Patent: *May 25, 2021

(54) SYSTEMS, METHODS, AND DEVICES FOR ANALYSIS OF GENETIC MATERIAL

(71) Applicant: CODONDEX LLC, Sherman Oaks, CA (US)

(72) Inventors: Kevin Bermeister, Sherman Oaks, CA (US); Xinghao Yu, Ashfield (AU)

(73) Assignee: CODONDEX LLC, Sherman Oaks, CA (US)

( * ) Notice: Subject to any disclaimer, the term of this patent is extended or adjusted under 35 U.S.C. 154(b) by 619 days.

This patent is subject to a terminal disclaimer.

(21) Appl. No.: 15/861,673

(22) Filed: Jan. 4, 2018

(65) Prior Publication Data

US 2018/0203975 A1     Jul. 19, 2018

Related U.S. Application Data

(63) Continuation-in-part of application No. 15/345,505, filed on Nov. 7, 2016, now Pat. No. 10,854,314, which is a continuation of application No. PCT/US2015/030478, filed on May 13, 2015.

(60) Provisional application No. 62/443,136, filed on Jan. 6, 2017, provisional application No. 61/993,846, filed on May 15, 2014, provisional application No. 62/015,492, filed on Jun. 22, 2014.

(51) Int. Cl.
| | |
|---|---|
| *G01N 33/48* | (2006.01) |
| *G01N 33/50* | (2006.01) |
| *G16B 30/00* | (2019.01) |
| *C12Q 1/6869* | (2018.01) |
| *G16B 50/00* | (2019.01) |

(52) U.S. Cl.
CPC ........... *G16B 30/00* (2019.02); *C12Q 1/6869* (2013.01); *G16B 50/00* (2019.02)

(58) Field of Classification Search
CPC ....... C12Q 1/6869; G16B 30/00; G16B 50/00
See application file for complete search history.

(56) References Cited

U.S. PATENT DOCUMENTS

| | | | | |
|---|---|---|---|---|
| 8,725,422 | B2 | 5/2014 | Halpern et al. | |
| 10,679,727 | B2 | 6/2020 | Ding et al. | |
| 10,854,314 | B2 * | 12/2020 | Bermeister | G16B 30/00 |
| 2004/0086861 | A1 * | 5/2004 | Omori | H03M 13/00 |
| | | | | 435/6.14 |
| 2005/0043896 | A1 * | 2/2005 | Braun | G16B 30/00 |
| | | | | 702/19 |
| 2006/0224329 | A1 * | 10/2006 | Roth | G16B 20/00 |
| | | | | 702/20 |
| 2009/0208955 | A1 | 8/2009 | Harlan et al. | |
| 2016/0188797 | A1 | 6/2016 | Chang et al. | |

FOREIGN PATENT DOCUMENTS

| | | |
|---|---|---|
| CN | 102762743 A | 10/2012 |
| CN | 103201744 A | 7/2013 |
| CN | 104699998 A | 6/2015 |
| WO | 2015081754 A1 | 3/2015 |
| WO | 2015175602 A1 | 11/2015 |

OTHER PUBLICATIONS

WIPO, International Preliminary Report on Patentability Chapter I received in International Application No. PCT/IB2018/050053, dated Feb. 2, 2018, (9p.).
Yipeng, "Softman Subject Analysis and Information Retrieval Technique", English Translation Beijing University of Posts and Telecommuncations Press, Aug. 2012, pp. 149-156.
Chinese Office Action received in Chinese Application No. 201880012087.0, dated Apr. 15, 2020, (12p.).
Gotoh, "Homology-based gene structure prediction: simplified matching algorithm using a translated codon (tron) and improved accuracy by allowing for long gaps," Bioinformatics, 2000,16.3: pp. 190-202.
Nagasaki et al., "Automated classification of alternative splicing and transcriptional initiation and construction of visual database of classified patterns," Bioinformatics, 2006, 22.10: pp. 1211-1216.
Gopalan et al. "Xpro: database of eukaryotic proteinencoding genes," Nucleic acids research, 2004, 32.suppl I: pp. D59-D63.
WIPO, International Preliminary Report on Patentability Chapter I, for PCT/US2015/030478, WIPO, dated Nov. 15, 2016, pp. 1-7.
WIPO, International Search Report, for PCT /US2015/030478, WIPO, dated Sep. 8, 2015, pp. 1-2.
WIPO, Written Opinion of the International Searching Authority, for PCT /US2015/030478, WIPO, dated Sep. 8, 2015, pp. 1-6.
WIPO, International Search Report, for PCT /IB2018/050053, WIPO, dated Feb. 12, 2018, pp. 1-3.
WIPO, Written Opinion of the International Searching Authority, for PCT /IB2018/050053, WIPO, dated Feb. 12, 2018, pp. 1-8.
USPTO, Office Action received in U.S. Appl. No. 15/345,505, dated Nov. 19, 2019, p. 7.
USPTO, Office Action received in U.S. Appl. No. 15/345,505, dated Apr. 3, 2019, p. 7.

(Continued)

*Primary Examiner* — Russell S Negin
(74) *Attorney, Agent, or Firm* — Siritzky Law, PLLC; Brian Siritzky

(57) ABSTRACT

A representation of a nucleic acid sequence encodes a particular gene having at least one intron. An intron signature value corresponding to the at least one intron is determined based on a first computational function applied to at least one portion of the representation of the nucleic acid sequence corresponding to the at least one intron. A protein signature value is determined, being based on a second computational function applied to a representation of a protein. In a database, an association is formed between the intron and protein signature values. This process is repeated for each of a plurality of nucleic acid sequences. Nucleic acid sequences in the database are ordered based on a sort of corresponding intron signature values. An ordering determined by the sort is used to determine or confirm a role or function of a portion of a given nucleic acid sequence.

25 Claims, 3 Drawing Sheets

Specification includes a Sequence Listing.

(56) References Cited

OTHER PUBLICATIONS

Levinson et al., Slipped-strand mispairing: A major mechanism for DNA sequence evolution. Molecular Biology and Evolution, vol. 4, 1987, pp. 203-221.
Search Report received in Chinese Application No. 201880012087.0, dated Apr. 15, 2020, (2p.).
"Command and Control Information Precision Service", Chen Honghui National Defense Industry Press, published Jul. 31, 2015, pp. 186-191 (cited as "A" reference in Search Report received in Chinese Application No. 201880012087.0, dated Apr. 15, 2020.
Second Chinese Office Action received in Chinese Application No. 201880012087.0, dated Jan. 20, 2021, (13p.).
EPO, Extended European search report and written opinion, European Patent Application No. 18736154.8, dated Oct. 28, 2020.
EPO, Supplementary European Search Report for EP 18736154.8, dated Oct. 20, 2020.

\* cited by examiner

| Signature | DNA Sequence ID. | Intron Seq. IDs. | Exon Seq. IDs. | Genetic Function(s) | Protein ID. |
|---|---|---|---|---|---|
| S0 | $ID_0$ | ID-I-0 ... | ID-E-0 ... | F0 ... | P0 |
| ⋮ | | | | | |
| $S_K$ | $ID_K$ | ID-I-K ... | IE-E-K ... | | $P_K$ |
| ⋮ | | | | | |
| $S_N$ | $IN_N$ | ID-I-N ... | ID-E-N ... | | $P_N$ |

FIG. 2A

| Sequence ID. | Sequence |
|---|---|
| S0 | Sequence #0 |
| ⋮ | ⋮ |
| $S_J$ | Sequence #J |

FIG. 2B

SYSTEMS, METHODS, AND DEVICES FOR ANALYSIS OF GENETIC MATERIAL

RELATED APPLICATION

This application claims priority from U.S. Provisional Patent application No. 62/443,136, filed Jan. 6, 2017, the entire contents of which are hereby fully incorporated herein by reference for all purposes.

This application is a continuation-in-part (CIP) of U.S. patent application Ser. No. 15/345,505, filed Nov. 7, 2016, issued as U.S. Pat. No. 10,854,314 on Dec. 1, 2020, which is a continuation of PCT/US2015/030478, filed May 13, 2015, which claims priority from (i) U.S. Provisional Patent Application No. 61/993,846, filed May 15, 2014; and (ii) U.S. Provisional Patent Application No. 62/015,492, filed Jun. 22, 2014, the entire contents of each of which are hereby fully incorporated herein by reference for all purposes.

SEQUENCE LISTING

The instant application contains a Sequence Listing which has been submitted electronically in ASCII format and is hereby incorporated by reference in its entirety. Said ASCII copy, created on Jan. 12, 2018, is named 4040-0008-R_SL.txt and is 33,077 bytes in size.

COPYRIGHT STATEMENT

This patent document contains material subject to copyright protection. The copyright owner has no objection to the reproduction of this patent document or any related materials in the files of the United States Patent and Trademark Office, but otherwise reserves all copyrights whatsoever.

SOURCE CODE APPENDIX

This application includes a source code appendix with example computer source code. The source code appendix is considered part of this application for all purposes.

FIELD OF THE INVENTION

This invention relates to genetic engineering and microbiology, and, more particularly, to systems, methods, and devices for analysis of genetic material such as nucleotide sequences.

SUMMARY

The present invention is specified in the claims as well as in the below description. The following summary is exemplary and not limiting. Presently preferred embodiments are particularly specified in the dependent claims and the description of various embodiments.

In one embodiment, a computer-implemented method, implemented by hardware in combination with software, may comprise obtaining a representation of a nucleic acid sequence. The nucleic acid sequence may encode a particular gene and the particular gene may encode a particular protein. The nucleic acid sequence may comprise at least one intron. The embodiment may also comprise determining an intron signature value corresponding to the intron, with the intron signature value being based on a first computational function applied to one or more portions of the representation of the nucleic acid sequence corresponding to the at least one intron. The embodiment may also comprise determining a protein signature value corresponding to the particular protein, with the protein signature value being based on a second computational function applied to a representation of the particular protein, and forming, in a database, an association between the intron signature value and the protein signature value.

In another aspect, the method may comprise repeating the above acts for each of a plurality of nucleic acid sequences.

In another aspect, the computer-implemented method may also comprise using the formed association between the intron signature value and the protein signature value to determine or confirm at least one aspect of a genetic function of a particular nucleic acid sequence.

In another aspect, the computer-implemented method may comprise using the formed association between the intron signature value and the protein signature value to determine or confirm at least one aspect of a genetic function of a particular nucleic acid sequence for each of a plurality of nucleic acid sequences.

In another embodiment, a computer-implemented method, implemented by hardware in combination with software, may comprise obtaining a representation of a nucleic acid sequence, with the nucleic acid sequence comprising multiple non-overlapping nucleic acid subsequences, with each of the nucleic acid subsequences encoding an amino acid. The embodiment may also comprise determining a particular amino acid encoded by a particular nucleic acid subsequence of the multiple non-overlapping nucleic acid subsequences. The particular nucleic acid subsequence may comprise a first nucleotide, a second nucleotide adjacent to the first nucleotide, and a third nucleotide adjacent to the second nucleotide, by considering a nucleotide pair consisting of: (i) the first nucleotide and the second nucleotide, or (ii) the second nucleotide and the third nucleotide.

In another embodiment, a computer-implemented method of encoding a nucleic acid sequence, the method implemented by hardware in combination with software, may comprise obtaining a representation of the nucleic acid sequence, with the nucleic acid sequence comprising multiple non-overlapping nucleic acid subsequences, with each nucleic acid subsequences encoding an amino acid. The embodiment may also comprise determining a plurality of subsequences of the nucleic acid sequence, with the plurality of subsequences determined by a binary counting of the nucleic acid sequence, and determining a digital signature for the nucleic acid sequence based on a computational hash function applied to the plurality of subsequences of the nucleic acid sequence.

In another aspect, the computer-implemented method may comprise using the digital signature for the nucleic acid sequence to determine or confirm at least one aspect of a genetic function of the nucleic acid sequence.

In another embodiment, a computer implemented method, implemented by hardware in combination with software, may comprise obtaining a particular character string, with the particular character string being a representation of a first one or more portions of a particular nucleic acid sequence. The particular nucleic acid sequence may comprise a second one or more portions that may encode a particular protein, with the first one or more portions of the particular nucleic acid sequence being distinct from the second one or more portions of the particular nucleic acid sequence. The embodiment may also comprise determining a plurality of hash values of a corresponding plurality of substrings associated with the particular character string, determining a signature value for the first one or more portions of the particular nucleic acid sequence based on the first plurality of hash values, and forming an association in a database between the signature value for the first one or more portions of the particular nucleic acid sequence and the particular protein. The embodiment may also comprise using the association formed between the signature value for the first one or more portions of the particular nucleic acid sequence and the particular protein to determine or confirm at least one aspect of a genetic function of the particular nucleic acid sequence.

In another aspect, the computer-implemented method may comprise also using other associations in the database between other signature values of other character strings to determine or confirm the at least one aspect of a genetic function of the particular nucleic acid sequence.

In yet another embodiment, a computer-implemented method, implemented by hardware in combination with software, may comprise determining a particular intron signature value corresponding to a particular intron, with the particular intron signature value being based on a first computational function applied to one or more portions of a representation of a particular nucleic acid sequence corresponding to the particular intron. The embodiment may also comprise determining a particular protein signature value corresponding to a particular protein, with the protein signature value being based on a second computational hash function applied to a representation of the particular protein, and adding a record to a database, with the record comprising a first field for the particular intron signature value and a second field for the particular protein signature value computational hash function applied to a representation of the particular protein. The database may comprise a plurality of records corresponding to a plurality of nucleic acid sequences, with each of the records comprising an intron signature value and a corresponding protein signature value, with each of the intron signature values having been determined for and based on the first computational function applied to a portion of a corresponding nucleic acid sequence, the corresponding nucleic acid sequence encoding a particular gene, and each of the protein signature values having been determined based on a second computational hash function applied to a representation of a protein associated with the corresponding nucleic acid sequence.

In another aspect, the computer-implemented method may comprise using information in the database to determine or confirm at least one aspect of a genetic function of the particular nucleic acid sequence.

In another embodiment, a non-transitory computer-readable recording medium storing one or more programs, which, when executed, may cause one or more processors to obtain a representation of a nucleic acid sequence, with the nucleic acid sequence encoding a particular gene and the particular gene encoding a particular protein. The nucleic acid sequence may comprise at least one intron. The embodiment may also comprise causing the one or more processors to determine an intron signature value corresponding to the at least one intron, with the intron signature value being based on a first computational function applied to one or more portions of the representation of the nucleic acid sequence corresponding to the at least one intron, and to determine a protein signature value corresponding to the particular protein, with the protein signature value being based on a second computational function applied to a representation of the particular protein. The embodiment may also comprise causing the one or more processors to form, in a database, an association between the intron signature value and the protein signature value.

In another aspect, the non-transitory computer-readable recording medium, storing one or more programs, which, when executed, may cause one or more processors to use the association between the intron signature value and the protein signature value to determine or confirm at least one aspect of a genetic function of a particular nucleic acid sequence.

In another embodiment, a non-transitory computer-readable recording medium storing one or more programs, which, when executed, may cause one or more processors to obtain a representation of a nucleic acid sequence, with the nucleic acid sequence comprising multiple non-overlapping nucleic acid subsequences, and with each of the nucleic acid subsequences encoding an amino acid. The embodiment may also comprise causing the one or more processors to determine a plurality of subsequences of the nucleic acid sequence, with the plurality of subsequences being determined by a binary counting of the nucleic acid sequence, and to determine a digital signature for the nucleic acid sequence based on a computational hash function applied to the plurality of subsequences of the nucleic acid sequence.

In another aspect, the non-transitory computer-readable recording medium, storing one or more programs, which, when executed, may cause one or more processors to use the digital signature for the nucleic acid sequence to determine or confirm at least one aspect of a genetic function of the nucleic acid sequence.

In another embodiment, a non-transitory computer-readable recording medium storing one or more programs, which, when executed, may cause one or more processors to obtain a particular character string, with the particular character string being a representation of a first one or more portions of a particular nucleic acid sequence, with the particular nucleic acid sequence comprising a second one or more portions that encode a particular protein, and with the first one or more portions of the particular nucleic acid sequence being distinct from the second one or more portions of the particular nucleic acid sequence. The embodiment may also comprise causing the one or more processors to determine a plurality of hash values of a corresponding plurality of substrings associated with the particular character string, and to determine a signature value for the first one or more portions of the particular nucleic acid sequence based on the first plurality of hash values. The embodiment may also comprise causing the one or more processors to form an association in a database between the signature value for the first one or more portions of the particular nucleic acid sequence and the particular protein, and to use the association to determine or confirm at least one aspect of a genetic function of the particular nucleic acid sequence.

In another aspect, the non-transitory computer-readable recording medium, storing one or more programs, which, when executed, may cause one or more processors to use other associations in the database between other signature values of other character strings to determine or confirm the at least one aspect of a genetic function of the particular nucleic acid sequence.

In another embodiment, a non-transitory computer-readable recording medium storing one or more programs, which, when executed, may cause one or more processors to determine a particular intron signature value corresponding to a particular at least one intron, with the particular intron signature value being based on a first computational function applied to one or more portions of a representation of a particular nucleic acid sequence corresponding to the particular at least one intron. The embodiment may also comprise causing the one or more processors to determine a particular protein signature value corresponding to a particular protein, with the protein signature value being based on a second computational hash function applied to a representation of the particular protein, and to add a record to a database, with the record comprising a first field for the particular intron signature value and a second field for the particular protein signature value. The database may comprise a plurality of records corresponding to a plurality of nucleic acid sequences, with each of the records comprising an intron signature value and a corresponding protein signature value, with each of the intron signature values having been determined for and based on the first computational function applied to a portion of a corresponding nucleic acid sequence, the corresponding nucleic acid sequence encoding a particular gene, and each of the protein signature values having been determined based on a second computational hash function applied to a representation of a protein associated with the corresponding nucleic acid sequence.

In another aspect, the non-transitory computer-readable recording medium, storing one or more programs, which, when executed, may cause one or more processors to use information in the database to determine or confirm at least one aspect of a genetic function of the particular nucleic acid sequence.

Other aspects of the invention are discussed herein.

Below, further numbered embodiments of the invention will be discussed.

1. A computer-implemented method, implemented by hardware in combination with software, the method comprising:

(A) obtaining a representation of a nucleic acid sequence, wherein the nucleic acid sequence encodes a particular gene and the particular gene encodes a particular protein, the nucleic acid sequence comprising at least one intron;

(B) determining an intron signature value corresponding to the at least one intron, the intron signature value being based on a first computational function applied to one or more portions of the representation of the nucleic acid sequence corresponding to the at least one intron;

(C) determining a protein signature value corresponding to the particular protein, the protein signature value being based on a second computational function applied to a representation of the particular protein; and (D) forming, in a database, an association between the intron signature value and the protein signature value.

2. The method according to the previous embodiment, further comprising: (E) repeating acts (A) to (D) for each of a plurality of nucleic acid sequences.

3. The method according to any of the previous embodiments further comprising: (F) using the association formed in (D) to determine or confirm at least one aspect of a genetic function of a particular nucleic acid sequence.

4. The method according to any of the previous embodiments further comprising: (F) using the association formed in (D) to determine or confirm at least one aspect of a genetic function of a particular nucleic acid sequence.

5. A computer-implemented method, implemented by hardware in combination with software, the method comprising:

(A) obtaining a representation of a nucleic acid sequence, the nucleic acid sequence comprising multiple non-overlapping nucleic acid subsequences, each of the nucleic acid subsequences encoding an amino acid;

(B) determining a particular amino acid encoded by a particular nucleic acid subsequence of the multiple non-overlapping nucleic acid subsequences, wherein the particular nucleic acid subsequence comprises a first nucleotide, a second nucleotide adjacent to the first nucleotide, and a third nucleotide adjacent to the second nucleotide, by considering a nucleotide pair consisting of: (i) the first nucleotide and the second nucleotide, or (ii) the second nucleotide and the third nucleotide.

6. A computer-implemented method of encoding a nucleic acid sequence, the method implemented by hardware in combination with software, the method comprising:

(A) obtaining a representation of the nucleic acid sequence, the nucleic acid sequence comprising multiple non-overlapping nucleic acid subsequences, each of the nucleic acid subsequences encoding an amino acid;

(B) determining a plurality of subsequences of the nucleic acid sequence, wherein the plurality of subsequences are determined by a binary counting of the nucleic acid sequence;

(C) determining a digital signature for the nucleic acid sequence based on a computational hash function applied to the plurality of subsequences of the nucleic acid sequence.

7. A method according to the previous embodiment further comprising: (D) using the digital signature for the nucleic acid sequence to determine or confirm at least one aspect of a genetic function of the nucleic acid sequence.

8. A computer implemented method, implemented by hardware in combination with software, the method comprising:

(A) obtaining a particular character string, the particular character string being representation of a first one or more portions of a particular nucleic acid sequence, wherein the particular nucleic acid sequence comprises a second one or more portions that encode a particular protein, the first one or more portions of the particular nucleic acid sequence being distinct from the second one or more portions of the particular nucleic acid sequence;

(B) determining a plurality of hash values of a corresponding plurality of substrings associated with the particular character string;

(C) determining a signature value for the first one or more portions of the particular nucleic acid sequence based on the first plurality of hash values;

(D) forming an association in a database between the signature value for the first one or more portions of the particular nucleic acid sequence and the particular protein; and (E) using the association formed in (D) to determine or confirm at least one aspect of a genetic function of the particular nucleic acid sequence.

9. A method according to the previous embodiment wherein the using in (E) also uses other associations in the database between other signature values of other character strings to determine or confirm the at least one aspect of a genetic function of the particular nucleic acid sequence.

10. A computer-implemented method, implemented by hardware in combination with software, the method comprising:

(A) determining a particular intron signature value corresponding to a particular at least one intron, the particular intron signature value being based on a first computational function applied to one or more portions of a representation of a particular nucleic acid sequence corresponding to the particular at least one intron;

(B) determining a particular protein signature value corresponding to a particular protein, the protein signature value being based on a second computational hash function applied to a representation of the particular protein;

(C) adding a record to a database, the record comprising a first field for the particular intron signature value and a second field for the particular protein signature value, wherein the database comprises a plurality of records corresponding to a plurality of nucleic acid sequences, each of the records comprising an intron signature value and a corresponding protein signature value, each of the intron signature values having been determined for and based on the first computational function applied to a portion of a corresponding nucleic acid sequence, the corresponding nucleic acid sequence encoding a particular gene, and each of the protein signature values having been determined based on a second computational hash function applied to a representation of a protein associated with the corresponding nucleic acid sequence.

11. A method according to the previous embodiment, further comprising: (D) using information in the database to determine or confirm at least one aspect of a genetic function of the particular nucleic acid sequence.

12. A non-transitory computer-readable recording medium storing one or more programs, which, when executed, cause one or more processors to, at least:

(a) obtain a representation of a nucleic acid sequence, wherein the nucleic acid sequence encodes a particular gene and the particular gene encodes a particular protein, the nucleic acid sequence comprising at least one intron;

(b) determine an intron signature value corresponding to the at least one intron, the intron signature value being based on a first computational function applied to one or more portions of the representation of the nucleic acid sequence corresponding to the at least one intron;

(c) determine a protein signature value corresponding to the particular protein, the protein signature value being based on a second computational function applied to a representation of the particular protein; and (d) form, in a database, an association between the intron signature value and the protein signature value.

13. The non-transitory computer-readable recording medium according to the previous embodiment, wherein the one or more programs, when executed, cause one or more processors to, at least: (f) use the association formed in (d) to determine or confirm at least one aspect of a genetic function of a particular nucleic acid sequence.

14. A non-transitory computer-readable recording medium storing one or more programs, which, when executed, cause one or more processors to, at least:

(a) obtain a representation of the nucleic acid sequence, the nucleic acid sequence comprising multiple non-overlapping nucleic acid subsequences, each of the nucleic acid subsequences encoding an amino acid;

(b) determine a plurality of subsequences of the nucleic acid sequence, wherein the plurality of subsequences are determined by a binary counting of the nucleic acid sequence;

(c) determine a digital signature for the nucleic acid sequence based on a computational hash function applied to the plurality of subsequences of the nucleic acid sequence.

15. The non-transitory computer-readable recording medium according to the previous embodiment, wherein the one or more programs, when executed, cause one or more processors to, at least: (d) use the digital signature for the nucleic acid sequence to determine or confirm at least one aspect of a genetic function of the nucleic acid sequence.

16. A non-transitory computer-readable recording medium storing one or more programs, which, when executed, cause one or more processors to, at least:

(a) obtain a particular character string, the particular character string being representation of a first one or more portions of a particular nucleic acid sequence, wherein the particular nucleic acid sequence comprises a second one or more portions that encode a particular protein, the first one or more portions of the particular nucleic acid sequence being distinct from the second one or more portions of the particular nucleic acid sequence;

(b) determine a plurality of hash values of a corresponding plurality of substrings associated with the particular character string;

(c) determine a signature value for the first one or more portions of the particular nucleic acid sequence based on the first plurality of hash values;

(d) form an association in a database between the signature value for the first one or more portions of the particular nucleic acid sequence and the particular protein; and (e) use the association formed in (d) to determine or confirm at least one aspect of a genetic function of the particular nucleic acid sequence.

17. The non-transitory computer-readable recording medium according to the previous embodiment, wherein the using the association in (e) also uses other associations in the database between other signature values of other character strings to determine or confirm the at least one aspect of a genetic function of the particular nucleic acid sequence.

18. A non-transitory computer-readable recording medium storing one or more programs, which, when executed, cause one or more processors to, at least:

(a) determine a particular intron signature value corresponding to a particular at least one intron, the particular intron signature value being based on a first computational function applied to one or more portions of a representation of a particular nucleic acid sequence corresponding to the particular at least one intron;

(b) determine a particular protein signature value corresponding to a particular protein, the protein signature value being based on a second computational hash function applied to a representation of the particular protein;

(c) add a record to a database, the record comprising a first field for the particular intron signature value and a second field for the particular protein signature value, wherein the database comprises a plurality of records corresponding to a plurality of nucleic acid sequences, each of the records comprising an intron signature value and a corresponding protein signature value, each of the intron signature values having been determined for and based on the first computational function applied to a portion of a corresponding nucleic acid sequence, the corresponding nucleic acid sequence encoding a particular gene, and each of the protein signature values having been determined based on a second computational hash function applied to a representation of a protein associated with the corresponding nucleic acid sequence.

19. The non-transitory computer-readable recording medium according to the previous embodiment, wherein the one or more programs, when executed, cause one or more processors to, at least: (d) use information in the database to determine or confirm at least one aspect of a genetic function of the particular nucleic acid sequence.

The above features along with additional details of the invention, are described further in the examples below, which are intended to further illustrate the invention but are not intended to limit its scope in any way.

BRIEF DESCRIPTION OF THE DRAWINGS

Objects, features, and characteristics of the present invention as well as the methods of operation and functions of the related elements of structure, and the combination of parts and economies of manufacture, will become more apparent upon consideration of the following description and the appended claims with reference to the accompanying drawings, all of which form a part of this specification.

FIGS. 2A and 2B show exemplary database organizations according to embodiments hereof and FIG. 3 is a schematic diagram of a computer system used in embodiments hereof.

DETAILED DESCRIPTION OF THE PRESENTLY PREFERRED EXEMPLARY EMBODIMENTS

Glossary and Abbreviations

Figure 1:
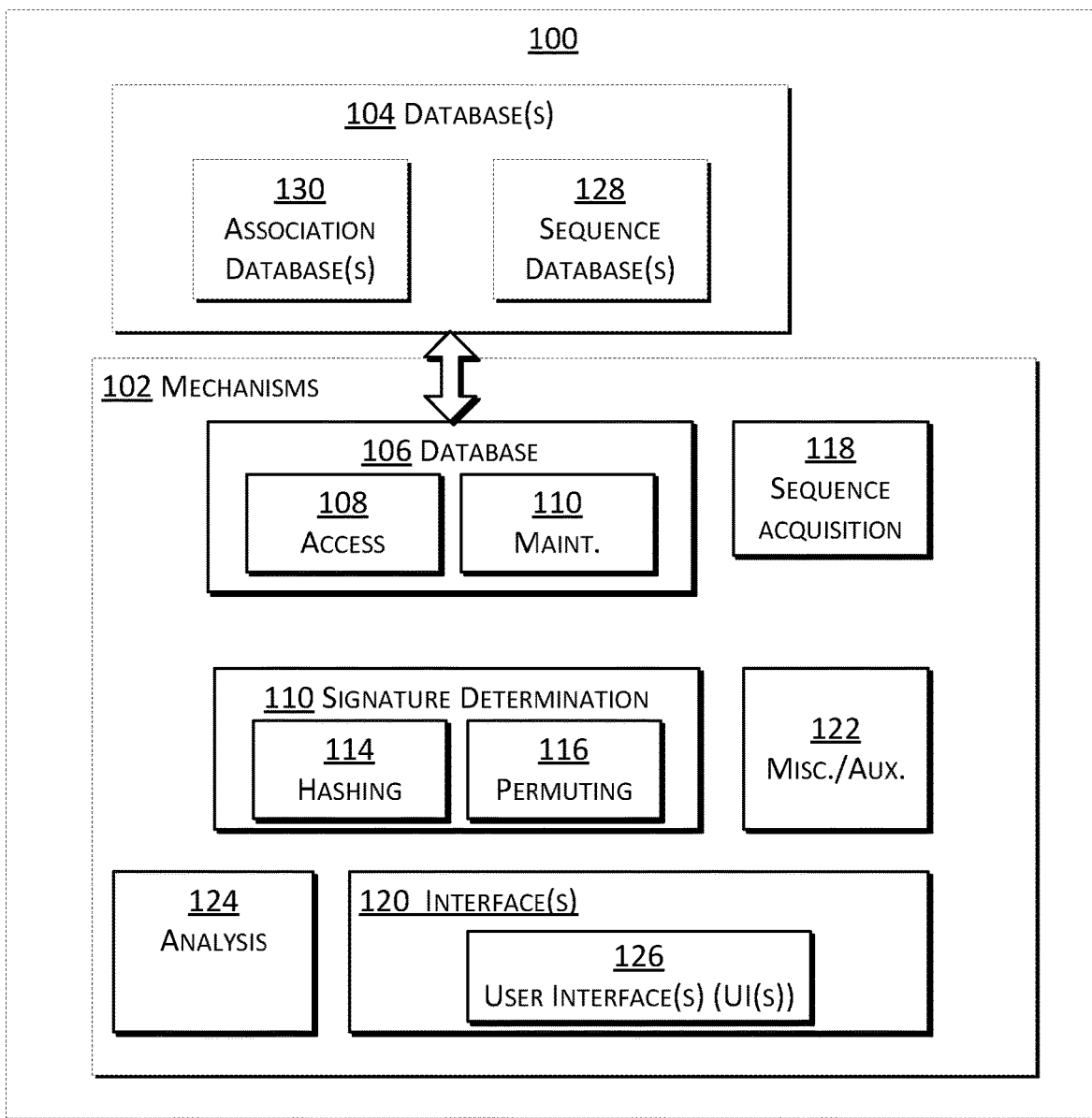
FIG. 1 shows an overview of a system according to embodiments hereof.

As used herein, unless used or described otherwise, the following terms or abbreviations have the following meanings:

"alphanumeric" means consisting of or using both letters and numbers;

"alphanumeric character" means a character that is either a letter or a number;

"alphanumeric string" means a character string consisting of letters and/or numbers;

"DNA" means deoxyribonucleic acid;

"DNA sequence" means a representation of the order in which the nucleotide bases are arranged within a nucleic acid sequence;

"exon" means a segment of a DNA or RNA molecule containing information coding for a protein or peptide sequence;

"FNV" means the Fowler-Noll-Vo hash function;

"genome" means the nuclear or organellar DNA content of a biological individual or sample;

"intron" means the part of a nucleotide sequence that's not an exon;

"RNA" means ribonucleic acid.

As used herein, the term "mechanism" refers to any device(s), process(es), service(s), or combination thereof. A mechanism may be implemented in hardware, software, firmware, using a special-purpose device, or any combination thereof. A mechanism may be integrated into a single device or it may be distributed over multiple devices. The various components of a mechanism may be co-located or distributed. The mechanism may be formed from other mechanisms. In general, as used herein, the term "mechanism" may thus be considered to be shorthand for the term device(s) and/or process(es) and/or service(s).

DESCRIPTION

Background and Overview

The background section of patent application no. PCT/US15/30478, filed May 13, 2015, published as WO 2015/175602 on Nov. 19, 2015, is fully incorporated herein for all purposes.

A DNA sequence is a sequence of nucleotide bases selected from the four nucleotide bases adenine (A), cytosine (C), guanine (G), and thymine (T). For notational convenience, and following convention, these bases are abbreviated herein as A, C, G, and T. That is, a DNA sequence S may be written as $s_1 s_2 \ldots s_k$, wherein each element $s_i$ in the sequence is selected from the set $\{A, C, T, G\}$.

As is well known, within the nucleus of a cell a DNA sequence takes the form of a double helix formed with base pairs. Within the base pairs, an adenine (A) nucleotide pairs with a thymine (T) nucleotide (and vice versa) and a cytosine (C) nucleotide pairs with a guanine (G) nucleotide (and vice versa).

As conventionally understood, a DNA sequence encodes a genetic function, and a DNA sequence may contain a gene, e.g., encoding for a protein.

There are twenty (20) amino acids (alanine, arginine, asparagine, aspartate, cysteine, glutamate, glutamine, glycine, histidine, isoleucine, leucine, lysine, methionine, phenylalanine, proline, serine, threonine, tryptophan, tyrosine, and valine) and all proteins are formed from combinations of these amino acids.

In order for a cell to perform a genetic function encoded in DNA (i.e., in a gene of the DNA) a copy of a portion of the DNA is made or transcribed onto messenger RNA (mRNA) to be passed from the nucleus into the cell. Transcription need not (and usually does not) read or copy the entire DNA, only the parts within the DNA that hold the information to perform the required function—e.g., to make the desired protein. In the case of protein production, a starting point is found in the DNA for the desired protein and then a transcript of the DNA is made (using RNA) up to an end point in the DNA.

The RNA copies at least a portion of the DNA using complementary bases according to the following rules:

| DNA | to | RNA |
| --- | --- | --- |
| T | → | A |
| C | → | G |
| G | → | C |
| A | → | U |

For RNA, the complement of A is U (Uracil), not thymine (T).

Thus an RNA sequence R may be written as $r_1 r_2 \ldots r_k$, wherein each $r_i$ is selected from the set $\{A, C, U, G\}$.

When DNA is transcribed to RNA each "T" is replaced by a "U", otherwise the sequence remains the same.

Before being sent from the nucleus into the cytoplasm of the cell, the RNA may undergo further processing, as explained here.

Recall that each gene may code for a specific protein and that the DNA that makes up a gene provides the code. However, not all of the DNA within a gene may directly code for proteins. The parts of DNA that codes directly for proteins are called exons. Non-coding portions of DNA that are within a gene and are between exons (coding portions) are referred to as introns. A gene may thus comprise one or exons interspersed with one or more introns. (E.g., as shown in the following:

<EXON$_1$><INTRON$_1$><EXON$_2$><INTRON$_2$><EXON$_3$><INTRON$_4$><EXON$_4$>

Processing of the transcribed RNA in the nucleus removes the introns so that the messenger RNA (mRNA) only contains the exons for a gene. E.g., for the above example, the mRNA would consist of:

<EXON-T$_1$><EXON-T$_2$><EXON-T$_3$><EXON-T$_4$> where <EXON-T$_k$> is the RNA sequence corresponding to the DNA sequence <EXON$_k$>.

The mRNA comprising the gene's concatenated exons is passed out of the cell's nucleus to the cytoplasm where translation of the mRNA to a protein occurs. Specifically, once the mRNA is made from transcription, the mRNA moves from the cell's nucleus into the cytoplasm where a ribosome assembles amino acids associated with another molecule known as tRNA that match the codon of mRNA sequences moving through the ribosome (as specified or encoded in the mRNA) according to the following process.

The bases in an RNA sequence may conveniently be grouped into triples called codons. As conventionally understood, one triple or codon—the first codon of the mRNA transcript—encodes a start codon. The most common start codon is AUG. A stop codon (or termination codon) is a nucleotide triplet within mRNA that signals termination of translation. There are several stop codons, specifically, in RNA: UAG, UAA, and UGA (in DNA: TAG, TAA, TGA).

Each codon (other than the start and stop codons) corresponds to one of the twenty amino acids (recall that there are twenty (20) amino acids and all proteins are formed from combinations of these amino acids). As there are four bases, there are sixty four possible codons (i.e., there are 64 triples that can be formed from the bases A, C, G, T (or A, C, G, U). As there are 20 amino acids and 64 possible codons that code for amino acids (less the start and stop codons), some amino acids are produced by more than one codon. For example, as shown in the table below, the four mRNA codons CCU, CCC, CCA, CCG all correspond to the amino acid proline. Similarly, the four mRNA codons GCU, GCC, GCA, GCG all correspond to the amino acid alanine. Notably, these codons differ only in their third nucleotide.

Translation from codon to protein occurs as follows:

1. In the cell's cytoplasm a ribosome recognizes the start codon in the mRNA and reads the mRNA one codon at a time.

2. An amino acid (one of the twenty) attached to an available tRNA molecule in the Cytoplasm is attracted by the ribosome and joined to form a sequence of amino acids based on the underlying mRNA codon's being processed through the ribosome, according to the rules in the following table, until a "stop" codon (ATG, ATT, ACT for DNA or UAA, UAG, UGA for RNA) is reached.

| Amino Acid | DNA Base Triplets | M-RNA Codons |
|---|---|---|
| Alanine | CGA, CGG, CGT, CGC | GCU, GCC, GCA, GCG |
| Arginine | GCA, GCG, GCT, GCC, TCT, TCC | CGU, CGC, CGA, CGG, AGA, AGG |
| asparagine | TTA, TTG | AAU, AAC |
| aspartate | CTA, CTG | GAU, GAC |
| Cysteine | ACA, ACG | UGU, UGC |
| glutamate | CTT, CTC | GAA, GAG |
| glutamine | GTT, GTC | CAA, CAG |
| glycine | CCA, CCG, CCT, CCC | GGU, GGC, GGA, GGG |
| histidine | GTA, GTG | CAU, CAC |
| isoleucine | TAA, TAG, TAT | AUU, AUC, AUA |
| leucine | AAT, AAC, GAA, GAG, GAT, GAC | UUA, UUG, CUU, CUC, CUA, CUG |
| lysine | TTT, TTC | AAA, AAG |
| methionine | TAC | AUG |
| phenylalanine | AAA, AAG | UUU, UUC |
| proline | GGA, GGG, GGT, GGC | CCU, CCC, CCA, CCG |
| serine | AGA, AGG, ACT, AGC, TCA, TCG | UCU, UCC, UCA, UCG, AGU, AGC |
| stop | ATG, ATT, ACT | UAA, UAG, UGA |
| threonine | TGA, TGG, TGT, TGC | ACU, ACC, ACA, ACG |
| tryptophan | ACC | UGG |
| tyrosine | ATA, ATG | UAU, UAC |
| valine | CAA, CAG, CAT, CAC | GUU, GUC, GUA, GUG |

The System

With reference now to FIG. 1, a system 100 according to embodiments hereof includes a number of mechanisms 102 interacting with one or more databases 104.

The exemplary mechanisms 102 may include database mechanism(s) 106, including database access mechanism(s) 108 and database maintenance mechanism(s) 110, signature determination mechanism(s) 112, which may include hashing mechanism(s) 114 and permuting mechanism(s) 116. Additionally, the mechanisms 102 may include sequence acquisition mechanism(s) 118, interface mechanism(s) 120, miscellaneous and auxiliary mechanism(s) 122, and analysis mechanism(s) 124. The interface mechanism(s) 120 may include user interface (UI) mechanism(s) 126.

The mechanisms may include the following mechanisms (described below): the "Pattern" mechanism; the "count" mechanisms; the "offset count, bigger length" mechanism; the "offset count, ignore length" mechanism; the iScore mechanism; the Signature mechanism; PhV mechanism; and the Position in Vector (PiV) mechanism.

The databases 104 may include one or more sequence databases 128 and one or more association databases 130.

With reference now to FIGS. 2A and 2B, the sequence database(s) 128 may include a mapping of sequence identifiers to corresponding sequences such as DNA sequences, RNA sequences, proteins, or the like. The sequences may correspond to introns or exons. The sequence identifiers may be arbitrarily assigned by the system.

The association database(s) 130 preferably include a mapping of signatures (described in greater detail below) to associated and corresponding DNA sequences (e.g., as identified by their sequence identifiers). The signatures may also map to one or more of: (i) one or more intron sequences (e.g., as identified by their sequence identifiers), (ii) one or more exon sequences (e.g., as identified by their sequence identifiers), and (iii) a protein. It should be appreciated that a particular signature may not map to all of the fields. It should also be appreciated that the database may include other mappings, e.g., from intron signatures to genetic functions or the like. The protein, if included, may be identified by a protein identifier that maps to a separate protein database (not shown) or it may be identified by a sequence identifier, mapping to the sequence database 128.

In the exemplary mappings in FIGS. 2A and 2B, the k-th row shows that signature Sk maps to DNA sequence identified by sequence identifier IDk (that maps to a DNA sequence in the sequence database 128 in FIG. 2B). Signature Sk may also map to (i) a sequence of one or more introns (identified by a corresponding one or more sequence identifiers ID-I-k . . . ); (ii) a sequence of one or more exons (identified by a corresponding one or more sequence identifiers ID-E-k . . . ); and (iii) a protein (identified by a corresponding sequence identifier Pk).

In FIGS. 2A and 2B the mappings are shown as tables. Those of ordinary skill in the art will realize and appreciate, upon reading this description, that these are merely exemplary representations of the databases and their mappings, and that different and/or other database organizations and/or representations may be used. It should be appreciated that the system is not limited by the particular database implementation or organization.

Data Representation

For computational purposes, e.g., in order to record and manipulate nucleotide (DNA and RNA) sequences, genetic sequencing data representing nucleotide sequences or peptide sequences are typically stored in a text format, such as FASTA or FASTQ, using single-letter codes to represent the nucleotides or amino acids. In the FASTA format, the bases adenine (A), cytosine (C), guanine (G), and thymine (T) are represented by the four ASCII letters "A", "C", "G", and "T", respectively. For RNA the base thymine (T) is replaced by the base uracil (U), represented by the letter "U". Thus the nucleotides that constitute DNA and RNA may be expressed in five distinct characters (A, G, C, T, or U for adenine, guanine, cytosine, thymine, or uracil, respectively).

However, if space and storage requirements are a concern, 3 bits may be used to represent each character.

As there are five values to be considered in each type of sequence, 3 bits are sufficient to store each sequence element (i.e., each nucleotide).

For some computational purposes a DNA (or RNA) sequence may be considered to be a character string with the characters selected from (and limited to) "A", "C", "G", and "T" (or "U" instead of "T" for RNA).

In conventional programming languages, such sequences may be represented as strings of characters.

Since arithmetic functions will be performed on these strings (e.g., to compute their hashes), each letter may also be assigned a numeric value. It should be appreciated that standard encoding of values for the letters (e.g., ASCII) may be used, as long as the encoding is consistent across the system. In some embodiments the letters may be assigned the values, e.g., 1, 2, 3, 4, and 5 for the letters "A", "C", "G", "T", and "U", respectively. In these embodiments the DNA sequence "AAGCGT" would correspond to the numerical sequence (or number) "113234", whereas the RNA sequence "AAGCGU" would correspond to the numerical sequence (or number) "113235". Using this approach, a DNA or RNA sequence may be directly manipulated and operated on arithmetically. Those of ordinary skill in the art will realize and appreciate, upon reading this description, that different and/or other encodings of DNA and RNA sequences may be used, and that some of these encodings will provide more efficient storage than others, and that some of these encodings will provide more efficient computation than others. It should also be appreciated that different coding and storage schemes may be used for different aspects of the system, again, as long as consistency is maintained. For example, it may be efficient to store data in one form and to operate on those data in another form. Those of ordinary skill in the art will understand how to select an encoding scheme that balances storage and computing requirements.

By convention the 20 amino acids are sometimes identified by their first three letters (e.g., "glu" for "glutamine", etc.), although for storage and computation purposes they are typically given one-letter abbreviations. The following table shows the standard 3 and 1 letter abbreviations for the twenty amino acids.

| Amino Acid | 3-Letter | 1-Letter |
|---|---|---|
| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |

-continued

| Amino Acid | 3-Letter | 1-Letter |
|---|---|---|
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Thus, as with DNA and RNA sequences, a protein may be represented by a character string (e.g., with the letters drawn from the alphabet in the 1-letter column in the table above). In order to operate arithmetically on sequences that represent proteins, each of the twenty characters may be assigned a different numeric value (e.g., 1 to 20 or the characters ASCII numeric value or some other value).

Mechanisms

For the purposes of this description, some of the mechanisms and algorithms are described as operating on alphanumeric strings (i.e., strings of characters). In some of the descriptions arbitrary characters are used to describe operation of aspects of some algorithms. As should be appreciated, the characters in the strings may represent DNA or RNA or protein sequences.

The "Pattern" Mechanism

A version of this pattern mechanism is described in our co-pending patent application no. PCT/US15/30478, the entire contents of which are hereby fully incorporated herein by reference for all purposes. An exemplary version of this procedure is described here.

For a given sequence or alphanumeric string $S = S_0 S_1 \ldots S_n$, where each element $S_i$ of the sequence is an alphabetic character: for each $S_i$ in $S$, the Pattern mechanism generates a set of subsequences that, inter alia, preserve sequences between letters in the original string $S = S_0 S_1 \ldots S_n$. The subsequence is preferably ordered and preferably includes the characters which are directly adjacent to $S_i$ in a forward direction. In a presently preferred implementation, the substring length is greater or equal than 8. Although this mechanism is described here for substring lengths greater than or equal to 8, it should be appreciated that other lengths, including zero (0) may be used. Thus, e.g., $Pattern_1(S)$ allows substrings of any length greater than or equal to 1. For the remainder of this description, unless stated otherwise, and without loss of generality, the function Pattern(S) refers to $Pattern_8(S)$.

$Pattern_8(S_i) = S_{i-7} \ldots S_i | S_{i-8} \ldots S_i | S_{i-9} \ldots S_i | \ldots | S_0 S_1 \ldots S_i$ Note that $Pattern_8(S)$ is an ordered sequence of zero or more substrings. For notational purposes, these substrings or sub-sequences are shown in the text separated by the bar ("|") character.

Consider the example where $S = G_0 T_1 G_2 G_3 G_4 C_5 C_6 C_7 A_8 G_9 A_{10} C_{11}$ (SEQ ID NO: 1)

For this example, as an aid to the explanation, each letter is also given a subscript showing its position in the string.

```
Pattern(G₀) = Empty (no subsequences longer than 8)

Pattern(C₇) = GTGGGCCC (i.e., G₀T₁G₂G₃G₄C₅C₆C₇)

Pattern(A₈) = TGGGCCCA | GTGGGCCCA (i.e.,
T₁G₂G₃G₄C₅C₆C₇A₈ and G₀T₁G₂G₃G₄C₅C₆C₇A₈).

Pattern(G₉) = GGGCCCAG | TGGGCCCAG | GTGGGCCCAG
(SEQ ID NO: 2)

. . .

Pattern(C₁₁) = GCCCAGAC | GGCCCAGAC | GGGCCCAGAC
(SEQ ID NO: 3) | TGGGCCCAGAC (SEQ ID NO: 4) |
GTGGGCCCAGAC (SEQ ID NO: 5)
```

The pattern for the entire string S is the ordered sequence of the patterns for each $S_i$ in S. For the example above, where
$S=G_0T_1G_2G_3G_4C_5C_6C_7A_8G_9A_{10}C_{11}$ (SEQ ID NO: 6)
P=Pattern(S)=Pattern($G_0$)|Pattern($C_7$)|Pattern($A_8$) . . . |Pattern($C_{11}$)

This corresponds to the following ordered sequence of fifteen strings:

```
                                               (SEQ ID NO: 7)
GTGGGCCC | TGGGCCCA | GTGGGCCCA | GGGCCCAG |
TGGGCCCAG | GTGGGCCCAG |

(SEQ ID NO: 8)
GGCCCAGA | GGGCCCAGA | TGGGCCCAGA |

(SEQ ID NO: 9)
GTGGGCCCAGA (SEQ ID NO: 10)
GCCCAGAC | GGCCCAGAC | GGGCCCAGAC |

(SEQ ID NO: 11)
TGGGCCCAGAC |

(SEQ ID NO: 12)
GTGGGCCCAGAC
```

The index into the ordered pattern sequence is referred to herein as the "offset," with the first element being element zero. Thus, in the example above, the first element, i.e., the element at offset=0, is $P_o$=GTGGGCCC=Pattern(S)$_0$, the second element, at offset=1, is $P_1$=TGGGCCCA, and so on, where $P_{14}$=GTGGGCCCAGAC (SEQ ID NO: 13).

As another example, for the string S'=1234567890ABCDEFGHIJ, P'=Pattern(S') corresponds to the following ordered sequence of strings:
12345678|23456789|123456789|34567890|23456789
0|1234567890|4567890A|34567890A|1234567890A
|1234567890A|567890AB|4567890AB|34567890AB
|234567890AB|1234567890AB|67890ABC|567890
ABC|4567890ABC|34567890ABC|234567890AB
C|1234567890ABC|7890ABCD|67890ABCD|567890
ABCD|4567890ABCD|34567890ABCD|234567890
ABCD|1234567890ABCD|890ABCDE|7890ABC
DE|67890ABCDE|567890ABCDE|4567890ABCD
E|34567890ABCDE|234567890ABCDE|12345678
90ABCDE|90ABCDEF|890ABCDEF|7890ABCDE
F|67890ABCDEF|567890ABCDEF|4567890ABCD
EF|34567890ABCDEF|234567890ABCDEF|123456
7890ABCDEF|0ABCDEFG|90ABCDEFG|890ABC
DEFG|7890ABCDEFG|67890ABCDEFG|567890A
BCDEFG|4567890ABCDEFG|34567890ABCDEF
G|234567890ABCDEFG|1234567890ABCDEFG|A
BCDEFGH|0ABCDEFGH|90ABCDEFGH|890AB
CDEFGH|7890ABCDEFGH|67890ABCDEFGH|56
7890ABCDEFGH|4567890ABCDEFGH|34567890
ABCDEFGH|234567890ABCDEFGH|1234567890
ABCDEFGH|BCDEFGHI|ABCDEFGHI|0ABCDE
FGHI|90ABCDEFGHI|890ABCDEFGHI|7890AB
CDEFGHI|67890ABCDEFGHI|567890ABCDEFG
HI|4567890ABCDEFGHI|34567890ABCDEFGHI|2
34567890ABCDEFGHI|1234567890ABCDEFGHI|
CDEFGHIJ|BCDEFGHIJ|ABCDEFGHIJ|0ABCDE
FGHIJ|90ABCDEFGHIJ|890ABCDEFGHIJ|7890A
BCDEFGHIJ|67890ABCDEFGHIJ|567890ABCDE
FGHIJ|4567890ABCDEFGHIJ|34567890ABCDEF
GHIJ|234567890ABCDEFGHIJ|1234567890ABC
DEFGHIJ In the above example, Pattern(S')=P' has 91 elements, with the element P'$_0$ at offset zero being "12345678", and the 91$^{st}$ element P'$_{90}$ at offset 90 being "1234567890ABCDEFGHIJ".

When the string S corresponds to a DNA or RNA or protein sequence, then Pattern(S) is a pattern for that DNA or RNA or protein sequence.

The "Count" Mechanisms

The count mechanisms operate on pattern sequences (i.e., on ordered alphanumeric sequences). Each count mechanism determines a count for each element of the sequence on which it operates. That is, if a sequence has k elements or subsequences (numbered from offset 0 to offset k−1), then that sequence will have k count values for each kind of count.

When the ordered sequence of elements corresponds to a pattern for a string, the count mechanism determines the count for that pattern.

When the ordered sequence of elements E corresponds to a pattern of a DNA or RNA or protein sequence, then Count(E) (for a particular count mechanism) provides corresponding count values for that DNA or RNA or protein sequence.

The "Offset Count, Bigger Length" Mechanism

For an ordered sequence of k elements E=[$E_0$, $E_1$ . . . $E_{k-1}$], the "offset count, bigger length" mechanism determines a corresponding vector or array of k count values, as follows:

For each sequence element $E_j$, for j=0 to k−1, (i.e., for subsequence $E_j$) start the count at zero (0), and then compare that subsequence $E_j$ to all the subsequences in the ordered sequence E. The count for the j-th element ($E_j$) increments by 1 if a target subsequence is longer than and contains compared subsequence ($E_j$).

For example, for the following ordered sequence E

```
                                               (SEQ ID NO: 14)
GTGGGCCC | TGGGCCCA | GTGGGCCCA | GGGCCCAG |
TGGGCCCAG | GTGGGCCCAG |
                                               (SEQ ID NO: 15)
GGCCCAGA | GGGCCCAGA | TGGGCCCAGA |
                                               (SEQ ID NO: 16)
GTGGGCCCAGA |
                                               (SEQ ID NO: 17)
GCCCAGAC | GGCCCAGAC | GGGCCCAGAC |
                                               (SEQ ID NO: 18)
TGGGCCCAGAC |
                                               (SEQ ID NO: 19)
GTGGGCCCAGAC
```

For the third element, $E_2$=Subsequence$_2$=GTGGGCCCA matches at offsets 5, 9 and 14 (GTGGGCCCAG (SEQ ID NO: 20), GTGGGCCCAGA (SEQ ID NO: 21), and GTGGGCCCAGAC (SEQ ID NO: 22)). To aid in this explanation, the matching parts of the sequence are underlined and in italics. Thus, in this example, Offset_Count_Bigger_Length(Subsequence$_2$)=3

When an ordered sequence of elements E corresponds to a pattern of a DNA or RNA or protein sequence, then Offset_Count_Bigger_Length(E) provides corresponding count values for that DNA or RNA or protein sequence.

The "Offset Count, Ignore Length" Mechanism

For an ordered sequence of k elements E[E$_0$, E$_1$ ... E$_{k-1}$], the "offset count, bigger length" mechanism determines a corresponding vector or array of k count values, as follows:

For each sequence element E$_j$, for j=0 to k−1, (i.e., for subsequence E) start the count at zero (0), and then, compare that subsequence to all the subsequences. The count for the j-th element (E$_j$) increments by 1 if either (i) the target subsequence contains the compared subsequence, or (ii) the compared subsequence contains target subsequence.

For example:

```
                                            (SEQ ID NO: 23)
0 GTGGGCCC | 1 TGGGCCCA | 2
GTGGGCCCA | 3 GGGCCCAG |
4 TGGGCCCAG | 5 GTGGGCCCAG |
```

```
                                            (SEQ ID NO: 24)
6 GGCCCAGA | 7 GGGCCCAGA | 8 TGGGCCCAGA |
```

```
                                            (SEQ ID NO: 25)
9 GTGGGCCCAGA |
```

```
                                            (SEQ ID NO: 26)
10 GCCCAGAC |11 GGCCCAGAC |12 GGGCCCAGAC |
```

```
                                            (SEQ ID NO: 27)
13 TGGGCCCAGAC |
```

```
                                            (SEQ ID NO: 28)
14 GTGGGCCCAGAC
```

For the third element, E$_2$=Subsequence$_2$=GTGGGCCCA matches at offsets 5, 9 and 14 (GTGGGCCCAG (SEQ ID NO: 29), GTGGGCCCAGA (SEQ ID NO: 30), and GTGGGCCCAGAC (SEQ ID NO: 31)), as with the Offset Count Bigger Length mechanism. In this case, Offset_Count_Ignore_Length also matches elements at offsets 0 and 1. Thus, in this example, Offset_Count_Ignore_Length(Subsequence$_2$)=6

It should be apparent that for an particular element of a sequence,
Offset_Count_Ignore_Length will always be greater than or equal to
Offset_Count_Bigger_Length.

When an ordered sequence of elements E corresponds to a pattern of a DNA or RNA or protein sequence, then Offset_Count_Ignore_Length(E) provides corresponding count values for that DNA or RNA or protein sequence.

The iScore Mechanism

For an ordered sequence of k elements E[E$_0$, E$_1$ ... E$_{k-1}$], the iScore mechanism determines a corresponding value for each element E$_E$, for j=0 to k−1, (i.e., for subsequence E$_E$) of the sequence, as follows:

iScore(E$_j$)=(Offset_Count_Ignore_Length(E$_j$)−Offset_Count_Bigger_Length(E$_j$))÷Length(E$_j$)

In the above example, for Subsequence$_2$=GTGGGCCCA, iScore(Subsequence$_2$=GTGGGCCCA)=(6−3)/9=0.33333

When the ordered sequence of elements corresponds to a pattern for a string, the iScore mechanism determines the iScores for that pattern.

When an ordered sequence of elements E corresponds to a pattern of a DNA or RNA or protein sequence, then iScore(E) provides corresponding iScore values for that DNA or RNA or protein sequence.

In the case of a nucleotide sequence, the iScore mechanism provides count of subsequence recurrence or inter-inclusiveness based on a one-nucleotide advance.

Example

This example shows the iScore values for the sequence

```
                                            (SEQ ID NO: 32)
S = "GTGCCCCCGGACTACATTTT".
```

The pattern mechanism applied to the string S (i.e., Pattern$_8$(S)=Pattern$_8$(GTGCCCCCGGACTACATTTT (SEQ ID NO: 33)) gives the following ordered sequence (with 91 elements):

```
                                            (SEQ ID NO: 34)
GTGCCCCC|TGCCCCCG|GTGCCCCCG|GCCCCCGG|TGCCCCGG|
GTGCCCCCGG|
```

```
                                            (SEQ ID NO: 35)
CCCCCGGA|GCCCCCGGA|TGCCCCCGGA|
```

```
                                            (SEQ ID NO: 36)
GTGCCCCCGGA|
```

```
                                            (SEQ ID NO: 37)
CCCCGGAC|CCCCCGGAC|GCCCCCGGAC|
```

```
                                            (SEQ ID NO: 38)
TGCCCCCGGAC|
```

```
                                            (SEQ ID NO: 39)
GTGCCCCCGGAC|CCCGGACT|CCCCGGACT|
```

```
                                            (SEQ ID NO: 40)
CCCCCGGACT|
```

```
                                            (SEQ ID NO: 41)
GCCCCCGGACT|
```

```
                                            (SEQ ID NO: 42)
TGCCCCCGGACT|
```

```
                                            (SEQ ID NO: 43)
GTGCCCCCGGACT|
```

```
                                            (SEQ ID NO: 44)
CCGGACTA|CCCGGACTA|CCCCGGACTA|
```

```
                                            (SEQ ID NO: 45)
CCCCCGGACTA|
```

```
                                            (SEQ ID NO: 46)
GCCCCCGGACTA|
```

```
                                            (SEQ ID NO: 47)
TGCCCCCGGACTA|
```

```
                                            (SEQ ID NO: 48)
GTGCCCCCGGACTA|
```

```
                                            (SEQ ID NO: 49)
CGGACTAC|CCGGACTAC|CCCGGACTAC|
```

```
                                            (SEQ ID NO: 50)
CCCCGGACTAC|
```

-continued

CCCCCGGACTAC| (SEQ ID NO: 51)

GCCCCCGGACTAC| (SEQ ID NO: 52)

TGCCCCCGGACTAC| (SEQ ID NO: 53)

GTGCCCCCGGACTAC| (SEQ ID NO: 54)

GGACTACA|CGGACTACA|CCGGACTACA| (SEQ ID NO: 55)

CCCGGACTACA| (SEQ ID NO: 56)

CCCCGGACTACA| (SEQ ID NO: 57)

CCCCCGGACTACA| (SEQ ID NO: 58)

GCCCCCGGACTACA| (SEQ ID NO: 59)

TGCCCCCGGACTACA| (SEQ ID NO: 60)

GTGCCCCCGGACTACA| (SEQ ID NO: 61)

GACTACAT|GGACTACAT|CGGACTACAT| (SEQ ID NO: 62)

CCGGACTACAT| (SEQ ID NO: 63)

CCCGGACTACAT| (SEQ ID NO: 64)

CCCCGGACTACAT| (SEQ ID NO: 65)

CCCCCGGACTACAT| (SEQ ID NO: 66)

GCCCCCGGACTACAT| (SEQ ID NO: 67)

TGCCCCCGGACTACAT| (SEQ ID NO: 68)

GTGCCCCCGGACTACAT| (SEQ ID NO: 69)

ACTACATT|GACTACATT|GGACTACATT| (SEQ ID NO: 70)

CGGACTACATT| (SEQ ID NO: 71)

CCGGACTACATT| (SEQ ID NO: 72)

CCCGGACTACATT| (SEQ ID NO: 73)

CCCCGGACTACATT| (SEQ ID NO: 74)

CCCCCGGACTACATT| (SEQ ID NO: 75)

GCCCCCGGACTACATT| (SEQ ID NO: 76)

TGCCCCCGGACTACATT| (SEQ ID NO: 77)

GTGCCCCCGGACTACATT| (SEQ ID NO: 78)

CTACATTT|ACTACATTT|GACTACATTT| (SEQ ID NO: 79)

GGACTACATTT| (SEQ ID NO: 80)

CGGACTACATTT| (SEQ ID NO: 81)

CCGGACTACATTT| (SEQ ID NO: 82)

CCCGGACTACATTT| (SEQ ID NO: 83)

CCCCGGACTACATTT| (SEQ ID NO: 84)

CCCCCGGACTACATTT| (SEQ ID NO: 85)

GCCCCCGGACTACATTT| (SEQ ID NO: 86)

TGCCCCCGGACTACATTT| (SEQ ID NO: 87)

GTGCCCCCGGACTACATTT| (SEQ ID NO: 88)

TACATTTT|CTACATTTT|ACTACATTTT| (SEQ ID NO: 89)

GACTACATTTT| (SEQ ID NO: 90)

GGACTACATTTT| (SEQ ID NO: 91)

CGGACTACATTTT| (SEQ ID NO: 92)

CCGGACTACATTTT| (SEQ ID NO: 93)

CCCGGACTACATTTT| (SEQ ID NO: 94)

CCCCGGACTACATTTT| (SEQ ID NO: 95)

CCCCCGGACTACATTTT| (SEQ ID NO: 96)

GCCCCCGGACTACATTTT| (SEQ ID NO: 97)

TGCCCCCGGACTACATTTT| (SEQ ID NO: 98)

GTGCCCCCGGACTACATTTT (SEQ ID NO: 99)

The following table shows the iScores for each element of $Pattern_8(S)$ (with the iScore values truncated to three decimal places, for convenience of display).

| Offset | Subsequence | SEQ ID NO: | Subsequence Length | Offset Count Bigger Length | Offset Count ignore Length | iScore |
|---|---|---|---|---|---|---|
| 0 | GTGCCCCC | | 8 | 12 | 13 | 0.125 |
| 1 | TGCCCCCG | | 8 | 23 | 24 | 0.125 |
| 2 | GTGCCCCCG | | 9 | 11 | 14 | 0.333 |
| 3 | G CCCCGG | | 8 | 32 | 33 | 0.125 |
| 4 | TGCCCCCGG | | 9 | 21 | 24 | 0.333 |
| 5 | GTGCCCCCGG | 34 | 10 | 10 | 16 | 0.600 |
| 6 | CCCCCGGA | | 8 | 39 | 40 | 0.125 |
| 7 | GCCCCCGGA | | 9 | 29 | 32 | 0.333 |
| 8 | TGCCCCCGGA | 35 | 10 | 19 | 25 | 0.600 |
| 9 | GTGCCCCCGGA | 36 | 11 | 9 | 19 | 0.909 |
| 10 | CCCCGGAC | | 8 | 44 | 45 | 0.125 |
| 11 | CCCCCGGAC | | 9 | 35 | 38 | 0.333 |
| 12 | GCCCCCGGAC | 37 | 10 | 26 | 32 | 0.600 |
| 13 | TGCCCCCGGAC | 38 | 11 | 17 | 27 | 0.909 |
| 14 | GTGCCCCCGGAC | 39 | 12 | 8 | 23 | 1.250 |
| 15 | CCCGGACT | | 8 | 47 | 48 | 0.125 |
| 16 | CCCCGGACT | | 9 | 39 | 42 | 0.333 |
| 17 | CCCCCGGACT | 40 | 10 | 31 | 37 | 0.600 |
| 18 | GCCCCCGGACT | 41 | 11 | 23 | 33 | 0.909 |
| 19 | TGCCCCCGGACT | 42 | 12 | 15 | 30 | 1.250 |
| 20 | GTGCCCCCGGACT | 43 | 13 | 7 | 28 | 1.615 |
| 21 | CCGGACTA | | 8 | 48 | 49 | 0.125 |
| 22 | CCCGGACTA | | 9 | 41 | 44 | 0.333 |
| 23 | CCCCGGACTA | 44 | 10 | 34 | 40 | 0.600 |
| 24 | CCCCCGGACTA | 45 | 11 | 27 | 37 | 0.909 |
| 25 | GCCCCCGGACTA | 46 | 12 | 20 | 35 | 1.250 |
| 26 | TGCCCCCGGACTA | 47 | 13 | 13 | 34 | 1.615 |
| 27 | GTGCCCCCGGACTA | 48 | 14 | 6 | 34 | 2.000 |
| 28 | CGGACTAC | | 8 | 47 | 48 | 0.125 |
| 29 | CCGGACTAC | | 9 | 41 | 44 | 0.333 |
| 30 | CCCGGACTAC | 49 | 10 | 35 | 41 | 0.600 |
| 31 | CCCCGGACTAC | 50 | 11 | 29 | 39 | 0.909 |
| 32 | CCCCCGGACTAC | 51 | 12 | 23 | 38 | 1.250 |
| 33 | GCCCCCGGACTAC | 52 | 13 | 17 | 38 | 1.615 |
| 34 | TGCCCCCGGACTAC | 53 | 14 | 11 | 39 | 2.000 |
| 35 | GTGCCCCCGGACTAC | 54 | 15 | 5 | 41 | 2.400 |
| 36 | GGACTACA | | 8 | 44 | 45 | 0.125 |
| 37 | CGGACTACA | | 9 | 39 | 42 | 0.333 |
| 38 | CCGGACTACA | 55 | 10 | 34 | 40 | 0.600 |
| 39 | CCCGGACTACA | 56 | 11 | 29 | 39 | 0.909 |
| 40 | CCCCGGACTACA | 57 | 12 | 24 | 39 | 1.250 |
| 41 | CCCCCGGACTACA | 58 | 13 | 19 | 40 | 1.615 |
| 42 | GCCCCCGGACTACA | 59 | 14 | 14 | 42 | 2.000 |
| 43 | TGCCCCCGGACTACA | 60 | 15 | 9 | 45 | 2.400 |
| 44 | GTGCCCCCGGACTACA | 61 | 16 | 4 | 49 | 2.813 |
| 45 | GACTACAT | | 8 | 39 | 40 | 0.125 |
| 46 | GGACTACAT | | 9 | 35 | 38 | 0.333 |
| 47 | CGGACTACAT | 62 | 10 | 31 | 37 | 0.600 |
| 48 | CCGGACTACAT | 63 | 11 | 27 | 37 | 0.909 |
| 49 | CCCGGACTACAT | 64 | 12 | 23 | 38 | 1.250 |
| 50 | CCCCGGACTACAT | 65 | 13 | 19 | 40 | 1.615 |
| 51 | CCCCCGGACTACAT | 66 | 14 | 15 | 43 | 2.000 |
| 52 | GCCCCCGGACTACAT | 67 | 15 | 11 | 47 | 2.400 |
| 53 | TGCCCCCGGACTACAT | 68 | 16 | 7 | 52 | 2.813 |
| 54 | GTGCCCCCGGACTACAT | 69 | 17 | 3 | 58 | 3.235 |
| 55 | ACTACATT | | 8 | 32 | 33 | 0.125 |
| 56 | GACTACATT | | 9 | 29 | 32 | 0.333 |
| 57 | GGACTACATT | 70 | 10 | 26 | 32 | 0.600 |
| 58 | CGGACTACATT | 71 | 11 | 23 | 33 | 0.909 |
| 59 | CCGGACTACATT | 72 | 12 | 20 | 35 | 1.250 |
| 60 | CCCGGACTACATT | 73 | 13 | 17 | 38 | 1.615 |
| 61 | CCCCGGACTACATT | 74 | 14 | 14 | 42 | 2.000 |
| 62 | CCCCCGGACTACATT | 75 | 15 | 11 | 47 | 2.400 |
| 63 | GCCCCCGGACTACATT | 76 | 16 | 8 | 53 | 2.813 |
| 64 | TGCCCCCGGACTACATT | 77 | 17 | 5 | 50 | 3.235 |
| 65 | GTGCCCCCGGACTACATT | 78 | 18 | 2 | 68 | 3.667 |
| 66 | CTACATTT | | 8 | 23 | 24 | 0.125 |
| 67 | ACTACATTT | | 9 | 21 | 24 | 0.333 |
| 68 | GACTACATTT | 79 | 10 | 19 | 25 | 0.600 |
| 69 | GGACTACATTT | 80 | 11 | 17 | 27 | 0.909 |
| 70 | CGGACTACATTT | 81 | 12 | 15 | 30 | 1.250 |
| 71 | CCGGACTACATTT | 82 | 13 | 13 | 34 | 1.615 |
| 72 | CCCGGACTACATTT | 83 | 14 | 11 | 39 | 2.000 |
| 73 | CCCCGGACTACATTT | 84 | 15 | 9 | 45 | 2.400 |
| 74 | CCCCCGGACTACATTT | 85 | 16 | 7 | 52 | 2.813 |
| 75 | GCCCCCGGACTACATTT | 86 | 17 | 5 | 60 | 3.235 |

-continued

| Offset | Subsequence | SEQ ID NO: | Subsequence Length | Offset Count Bigger Length | Offset Count ignore Length | iScore |
|---|---|---|---|---|---|---|
| 76 | TGCCCCCGGACTACATTT | 87 | 18 | 3 | 59 | 3.667 |
| 77 | GTGCCCCCGGACTACATTT | 88 | 19 | 1 | 79 | 4.105 |
| 78 | TACATTTT | | 8 | 12 | 13 | 0.125 |
| 79 | CTACATTTT | | 9 | 11 | 14 | 0.333 |
| 80 | ACTACATTTT | 89 | 10 | 10 | 16 | 0.600 |
| 81 | GACTACATTTT | 90 | 11 | 9 | 19 | 0.909 |
| 82 | GGACTACATTTT | 91 | 12 | 8 | 23 | 1.250 |
| 83 | CGGACTACATTTT | 92 | 13 | 7 | 28 | 1.615 |
| 84 | CCGGACTACATTTT | 93 | 14 | 6 | 34 | 2.000 |
| 85 | CCCGGACTACATTTT | 94 | 15 | 5 | 41 | 2.400 |
| 86 | CCCCGGACTACATTTT | 95 | 16 | 4 | 49 | 2.813 |
| 87 | CCCCCGGACTACATTTT | 96 | 17 | 3 | 58 | 3.235 |
| 88 | GCCCCCGGACTACATTTT | 97 | 18 | 2 | 68 | 3.667 |
| 89 | TGCCCCCGGACTACATTTT | 98 | 19 | 1 | 79 | 4.105 |
| 90 | GTGCCCCCGGACTACATTTT | 99 | 20 | 0 | 91 | 4.550 |

Complementary Subsequences

For a give DNA sequence (S), the complementary sequence (C) is a sequence formed using complementary bases according to the following rules:

| DNA | to | RNA |
|---|---|---|
| T | → | A |
| C | → | G |
| G | → | C |
| A | → | U |

Note that on the RNA the complement of A is U (Uracil), not thymine (T).

An RNA sequence R may be written as $r_1 r_2 \ldots r_k$, wherein each $r_i$ is selected from the set {A, C, U, G}. When DNA is transcribed to RNA each "T" is replaced by a "U", otherwise the sequence remains the same.

For example, the complementary sequence of "GTAAGCCT" is "AGGCTTAC."

For a given sequence S, the reverse complementary sequence of S is the complement of the reverse of S.

In embodiments hereof, the system maintains a count the occurrence of all subsequences that include any subsequence's complement.

The Signature Mechanism

The signature mechanism provides a signature value of an alphanumeric string, where the value may be used, e.g., as a database index or key for that string.

In presently preferred implementations the signature ($V_S$) for a particular sequence (represented, e.g., as a character string $S=s_1 s_2 \ldots s_n$) is obtained as follows:

1: Generate sequence (or ordered list) of sub strings of S using, e.g., the pattern function (described above, e.g., Pattern$_8$(S))
2: Generate sequence of hash values, one for each element of the ordered list of substrings.
3: Generate signature $F_S$ as a function of the sequence of hash values of the substrings. Preferably the signature $F_S$ is a hash of the concatenated sequence of hash values of the substrings.
4: Repeat steps 2 to 4 for the reverse (R) of string S to obtain a signature $R_S$ of the reverse string R.
5: Generate $V_S$ as a function of $F_S$ and $R_S$ (e.g., $F_S + R_S$)
Where the sequence S corresponds to an intron, the value
$V_S$=signature (S)
is a signature for that intron.
Where the sequence S corresponds to an exon, the value
$V_S$=signature (S)
is a signature for that exon.
Where the sequence S corresponds to a protein, the value
$V_S$=signature (S)
is a signature for that protein.
Where the sequence S corresponds to a plurality of introns in a gene, the value $V_S$ is an intron signature for that gene. For example, suppose a gene has the form:
<EXON$_1$><INTRON$_1$><EXON$_2$><INTRON$_2$><EXON$_3$><INTRON$_3$><EXON$_4$>
Then the introns for that gene are:
<INTRON$_1$><INTRON$_2$><INTRON$_3$>
and $V_S$=signature (<INTRON$_1$><INTRON$_2$><INTRON$_3$>) may be considered an intron signature of the gene.

In some embodiments, the hashes of the reverse of the string may be omitted (in 4), and the value $V_S$ is a function of $F_S$, e.g., $V_S = F_S$. Other information, e.g., the length of the string S, may be used to determine Vs.

A requirement of the signature function is that two identical strings have the same signature.

As is well known, a hash function is a function that converts its input into a numeric value, called its hash value. Preferably the hash function is a non-cryptographic hash function such as FNV (e.g., FNV1-64 Bit). Exemplary source code for the FNV hashing function (in the Ruby programming language) is shown in Appendix I to Application PCT/US15/30478, which as been incorporated into this application for all purposes.

For example, using the exemplary FNV source code in Appendix I to Application PCT/US15/30478, the function call puts FNV. calculate("ABCDE") generates the hash value 8130071842065240010 corresponding to the string "ABCDE".

It should be appreciated that any hash function may be used, and that FNV is merely provided by way of example. Furthermore, while any hash function may be used, preferred embodiments hereof use two-way or reversible hash functions. In preferred embodiments the same hash function must be used for all independent entities in the string to produce the result.

PhV Mechanism

Recall that a given gene has a number of transcripts, some of which may be protein coding. For example, MEN1 has 15 protein-coding transcripts and BRCA1 has 25 are protein-coding transcripts.

For a given gene with k protein-coding transcripts ($T_1$, $T_2$ ... $T_k$), the PhV mechanism generates an ordered sequence (or vector) of k values, where the i-th value is signature($T_i$). Thus, e.g., for the MEN1 gene with 15 protein-coding transcripts, PhV(MEN1)=[signature($T_1$), signature($T_2$), ... signature($T_k$)]

Position in Vector (PiV) Mechanism

For a given gene G with m protein-coding transcripts (m≥1), a Pattern mechanism (e.g., $Pattern_8$) is applied to the intron values for each of the m transcripts, giving m ordered sequences of elements, one for the intron(s) of each transcript.

For the purposes of this description, and without loss of generality, the ordered sequence of elements for the intron(s) of the i-th transcript is referred to here as $E_i$. If a gene has m protein-coding transcripts, then m ordered sequences of transcripts ($E_1$, $E_2$ ... $E_m$) are generated.

For each of the m ordered sequences of transcripts ($E_1$, $E_2$ ... $E_m$), the iScore mechanism is applied to the components of Ei, giving, for each element of Ei (i.e., at each offset in Ei) a corresponding iScore.

The Position in Vector (PiV) mechanism determines an ordered sequence (or vector) of vector index values for each offset of an intron subsequence. The vector index values for each PiV are in the range 1 to m for a gene that has m protein-coding transcripts (m≥1).

The protein hash vector mechanism (described above), applied to the proteins of the gene, gives a vector with m protein signatures (sometimes also referred to as protein hashes).

For a particular intron subsequence (e.g., $E_i$), at a given offset (e.g., offset=j), the PiV for the given offset j is determined by comparing the iScore values for each of the other intron subsequences for this gene at the given offset j. If the sorted iScore values match the protein hash vector for the gene under consideration, then the PiV uses those indices. Since iValues may be the same for multiple indices, some PiV indices with the same iValue may be reordered. On the other hand, if the sorted iScore values do not match the protein hash vector (PhV) for the gene under consideration, then the PiV uses a max-order for the indices, where the max-order tries to maximize the match of the order of the PhV.

Position in Vector (PiV) is determined using subsequence hashes at the same nucleotide from zero. The ordered subsequence hashes are compared to the original position of the transcript protein hash, the constant of each transcript in the set being analyzed.

The cumulative PiV is a count, for all subsequences, of the number of times they are assigned to each PiV.

It should be appreciated that PhV and PiV are each relativity measures of all transcripts at an offset. Both maximize the ordering of transcripts based on the same application of ordering rules. PiV begins using iScore, PhV protein hash. Protein is the constant for each transcript at all offsets. Using its hash causes each transcript at any offset to start in the same order. Whereas, iScore is a variable that potentially starts each transcript in a different order at each offset.

The rules of max-order for transcripts of an offset may be summarized (for some embodiments) as: PiV is initially grouped by iScore, PhV by hash. Each are subsequently reordered within their sub-group boundaries by the reciprocal PhV or iScore to obtain a final ordering that is maximized at the offset.

Our objective is to discover transcripts at offsets that retain the same position in each of their respective vectors, because sequence text of transcripts that retain position at offsets, using both methods exposes a dominant subset.

Example

Recall that MEM1 has 15 transcripts (ENST00000413626; ENST00000429702; ENST00000394376; ENST00000377326; ENST00000450708; ENST00000377313; ENST00000424912; ENST00000377321; ENST00000315422; ENST00000443283; ENST00000337652; ENST00000312049; ENST00000377316; ENST00000440873; ENST00000394374).

For the MEM1 gene, at offset 1,000, the subsequences for the introns of each transcript are shown in the following table:

| Sequence | Compared Sequence | SEQ ID NO: |
|---|---|---|
| ENST00000413626 | GCACAGTCGTAGAGAGGG | 100 |
| ENST00000429702 | GGGCACGCTTCCTGCCTG | 101 |
| ENST00000394376 | CCAGCTAAAGCGGCTGAA | 102 |
| ENST00000377326 | CCCACTTCTTCAAAACCC | 103 |
| ENST00000450708 | AGGACTCTCCTTGGGGTT | 104 |
| ENST00000377313 | CCCTCCATGGTTTACAGA | 105 |
| ENST00000424912 | CCAGCTAAAGCGGCTGAA | 106 |
| ENST00000377321 | GGGGTTTGGGGGCTTGAC | 107 |
| ENST00000315422 | GAGCTGTGCGTGTGTCGG | 108 |
| ENST00000443283 | GACCCTAGGGGCGGGACT | 109 |
| ENST00000337652 | GGGCACGCTTCCTGCCTG | 110 |
| ENST00000312049 | GACCCTAGGGGCGGGACT | 111 |
| ENST00000377316 | CCCACTTCTTCAAAACCC | 112 |
| ENST00000440873 | GGGGTTTGGGGGCTTGAC | 113 |
| ENST00000394374 | GAGCTGTGCGTGTGTCGG | 114 |

The following table is an iScore matrix for the MEM1 gene at offset 1,000.

| Sequence | iScore | Position in iScore Vector |
|---|---|---|
| ENST00000413626 | 3.722222222 | 13 |
| ENST00000429702 | 3.666666667 | 10 |
| ENST00000394376 | 3.666666667 | 7 |
| ENST00000377326 | 3.666666667 | 12 |
| ENST00000450708 | 3.666666667 | 2 |
| ENST00000377313 | 3.666666667 | 5 |
| ENST00000424912 | 3.666666667 | 9 |
| ENST00000377321 | 3.666666667 | 8 |
| ENST00000315422 | 3.666666667 | 11 |
| ENST00000443283 | 3.777777778 | 14 |
| ENST00000337652 | 3.666666667 | 4 |
| ENST00000312049 | 3.777777778 | 15 |
| ENST00000377316 | 3.666666667 | 1 |
| ENST00000440873 | 3.666666667 | 3 |
| ENST00000394374 | 3.666666667 | 6 |

Example

For the BRCA1 gene at offset 7,000, the subsequences for the introns of each transcript are shown in the following table:

| Sequence | Compared Sequence | SEQ ID NO: |
|---|---|---|
| ENST00000477152 | GGACAGGGGCCCAAGTGATGCTCTGGGGTACTGGCGTGGGAGAGTGGATTTCCGAAGCTGACAGATGGGTATTCTTTGACGGGGGGTAGGGGCGGAACCTGAGA | 115 |
| ENST00000493795 | GGAAAGGGACAGGGGGCCCAAGTGATGCTCTGGGGTACTGGCGTGGGAGAGTGGATTTCCGAAGCTGACAGATGGGTATTCTTTGACGGGGGGTAGGGGCGGAAC | 116 |
| ENST00000487825 | GAATGACACTCAAGTGCTGTCCATGAAAACTCAGGAAGTTTGCACAATTACTTTCTATGACGTGGTGATAAGACCTTTTAGTCTAGGTTAATTTTAGTTCTGTAT | 117 |
| ENST00000461221 | GGGGCGGAACCTGAGAGGCGTAAGGCGTTGTGAACCCTGGGGAGGGGGGCAGTTTGTAGGTCGCGAGGGAAGCGCTGAGGATCAGGAAGGGGGCACTGAGTGTCC | 118 |
| ENST00000357654 | GGACAGGGGCCCAAGTGATGCTCTGGGGTACTGGCGTGGGAGAGTGGATTTCCGAAGCTGACAGATGGGTATTCTTTGACGGGGGGTAGGGGCGGAACCTGAGA | 119 |
| ENST00000471181 | GGACAGGGGCCCAAGTGATGCTCTGGGGTACTGGCGTGGGAGAGTGGATTTCCGAAGCTGACAGATGGGTATTCTTTGACGGGGGGTAGGGGCGGAACCTGAGA | 120 |
| ENST00000351666 | ATTAATTTGGGATTCCTATGATTATCTCCTATGCAAATGAACAGAATTGACCTTACATACTAGGGAAGAAAAGACATGTCTAGTAAGATTAGGCTATTGTAATTG | 121 |
| ENST00000461798 | GGAAAGGGACAGGGGGCCCAAGTGATGCTCTGGGGTACTGGCGTGGGAGAGTGGATTTCCGAAGCTGACAGATGGGTATTCTTTGACGGGGGGTAGGGGCGGAAC | 122 |
| ENST00000493919 | GGAAAGGGACAGGGGGCCCAAGTGATGCTCTGGGGTACTGGCGTGGGAGAGTGGATTTCCGAAGCTGACAGATGGGTATTCTTTGACGGGGGGTAGGGGCGGAAC | 123 |
| ENST00000489037 | GGGGCGGAACCTGAGAGGCGTAAGGCGTTGTGAACCCTGGGGAGGGGGGCAGTTTGTAGGTCGCGAGGGAAGCGCTGAGGATCAGGAAGGGGGCACTGAGTGTCC | 124 |
| ENST00000412061 | CTTAACAGGCACTGAAAAGAGAGTGGGTAGATACAGTACTGTAATTAGATTATTCTGAAGACCATTTGGGACCTTTACAACCCACAAAATCTCTTGGCAGAGTTA | 125 |
| ENST00000468300 | GGAAAGGGACAGGGGGCCCAAGTGATGCTCTGGGGTACTGGCGTGGGAGAGTGGATTTCCGAAGCTGACAGATGGGTATTCTTTGACGGGGGGTAGGGGCGGAAC | 126 |
| ENST00000470026 | GGGGCGGAACCTGAGAGGCGTAAGGCGTTGTGAACCCTGGGGAGGGGGGCAGTTTGTAGGTCGCGAGGGAAGCGCTGAGGATCAGGAAGGGGGCACTGAGTGTCC | 127 |
| ENST00000478531 | GGAAAGGGACAGGGGGCCCAAGTGATGCTCTGGGGTACTGGCGTGGGAGAGTGGATTTCCGAAGCTGACAGATGGGTATTCTTTGACGGGGGGTAGGGGCGGAAC | 128 |
| ENST00000497488 | GGACAGGGGCCCAAGTGATGCTCTGGGGTACTGGCGTGGGAGAGTGGATTTCCGAAGCTGACAGATGGGTATTCTTTGACGGGGGGTAGGGGCGGAACCTGAGA | 129 |
| ENST00000494123 | GGAAAGGGACAGGGGGCCCAAGTGATGCTCTGGGGTACTGGCGTGGGAGAGTGGATTTCCGAAGCTGACAGATGGGTATTCTTTGACGGGGGGTAGGGGCGGAAC | 130 |
| ENST00000473961 | GAATGACACTCAAGTGCTGTCCATGAAAACTCAGGAAGTTTGCACAATTACTTTCTATGACGTGGTGATAAGACCTTTTAGTCTAGGTTAATTTTAGTTCTGTAT | 131 |
| ENST00000354071 | GGACAGGGGCCCAAGTGATGCTCTGGGGTACTGGCGTGGGAGAGTGGATTTCCGAAGCTGACAGATGGGTATTCTTTGACGGGGGGTAGGGGCGGAACCTGAGA | 132 |

-continued

| Sequence | Compared Sequence | SEQ ID NO: |
|---|---|---|
| ENST00000461574 | TGTTTGCCCCAGTCTATTTATAGAAGTGAGC TAAATGTTTATGCTTTTGGGGAGCACATTTT ACAAATTTCCAAGTATAGTTAAAGGAACTGC TTCTTAAACTTG | 133 |
| ENST00000492859 | GGACAGGGGGCCCAAGTGATGCTCTGGGGTA CTGGCGTGGGAGAGTGGATTTCCGAAGCTGA CAGATGGGTATTCTTTGACGGGGGGTAGGGG CGGAACCTGAGA | 134 |
| ENST00000346315 | GGAAAGGGACAGGGGGCCCAAGTGATGCTCT GGGGTACTGGCGTGGGAGAGTGGATTTCCGA AGCTGACAGATGGGTATTCTTTGACGGGGGG TAGGGGCGGAAC | 135 |
| ENST00000352993 | GGACAGGGGGCCCAAGTGATGCTCTGGGGTA CTGGCGTGGGAGAGTGGATTTCCGAAGCTGA CAGATGGGTATTCTTTGACGGGGGGTAGGGG CGGAACCTGAGA | 136 |
| ENST00000586385 | GGGGCGGAACCTGAGAGGCGTAAGGCGTTGT GAACCCTGGGGAGGGGGCAGTTTGTAGGTC GCGAGGGAAGCGCTGAGGATCAGGAAGGGGG CACTGAGTGTCC | 137 |
| ENST00000591849 | GGACAGGGGGCCCAAGTGATGCTCTGGGGTA CTGGCGTGGGAGAGTGGATTTCCGAAGCTGA CAGATGGGTATTCTTTGACGGGGGGTAGGGG CGGAACCTGAGA | 138 |
| ENST00000476777 | GGACAGGGGGCCCAAGTGATGCTCTGGGGTA CTGGCGTGGGAGAGTGGATTTCCGAAGCTGA CAGATGGGTATTCTTTGACGGGGGGTAGGGG CGGAACCTGAGA | 139 |
| ENST00000309486 | GGAAAGGGACAGGGGGCCCAAGTGATGCTCT GGGGTACTGGCGTGGGAGAGTGGATTTCCGA AGCTGACAGATGGGTATTCTTTGACGGGGGG TAGGGGCGGAAC | 140 |
| ENST00000484087 | GAATGACACTCAAGTGCTGTCCATGAAAACT CAGGAAGTTTGCACAATTACTTTCTATGACG TGGTGATAAGACCTTTTAGTCTAGGTTAATT TTAGTTCTGTAT | 141 |
| ENST00000491747 | GGAAAGGGACAGGGGGCCCAAGTGATGCTCT GGGGTACTGGCGTGGGAGAGTGGATTTCCGA AGCTGACAGATGGGTATTCTTTGACGGGGGG TAGGGGCGGAAC | 143 |
| ENST00000591534 | GGACAGGGGGCCCAAGTGATGCTCTGGGGTA CTGGCGTGGGAGAGTGGATTTCCGAAGCTGA CAGATGGGTATTCTTTGACGGGGGGTAGGGG CGGAACCTGAGA | 144 |

The following table is an iScore matrix for the BRCA1 gene at offset 7,000.

| Sequence | iScore | Position in iScore Vector |
|---|---|---|
| ENST00000477152 | 46.2285714285714 | 18 |
| ENST00000493795 | 46.2285714285714 | 21 |
| ENST00000487825 | 46.2 | 2 |
| ENST00000461221 | 46.2190476190476 | 9 |
| ENST00000357654 | 46.2285714285714 | 13 |
| ENST00000471181 | 46.2285714285714 | 27 |
| ENST00000351666 | 46.2380952380952 | 29 |
| ENST00000461798 | 46.2285714285714 | 10 |
| ENST00000493919 | 46.2285714285714 | 26 |
| ENST00000489037 | 46.2190476190476 | 7 |
| ENST00000412061 | 46.2095238095238 | 5 |
| ENST00000468300 | 46.2285714285714 | 12 |
| ENST00000470026 | 46.2190476190476 | 6 |
| ENST00000478531 | 46.2285714285714 | 20 |
| ENST00000497488 | 46.2285714285714 | 25 |
| ENST00000494123 | 46.2285714285714 | 14 |
| ENST00000473961 | 46.2 | 3 |
| ENST00000354071 | 46.2285714285714 | 24 |
| ENST00000461574 | 46.2 | 4 |
| ENST00000492859 | 46.2285714285714 | 22 |
| ENST00000346315 | 46.2285714285714 | 28 |
| ENST00000352993 | 46.2285714285714 | 23 |
| ENST00000586385 | 46.2190476190476 | 8 |
| ENST00000591849 | 46.2285714285714 | 16 |
| ENST00000476777 | 46.2285714285714 | 11 |
| ENST00000309486 | 46.2285714285714 | 17 |
| ENST00000484087 | 46.2 | 1 |
| ENST00000491747 | 46.2285714285714 | 15 |
| ENST00000591534 | 46.2285714285714 | 19 |

Computing

Programs that implement such methods (as well as other types of data) may be stored and transmitted using a variety of media (e.g., computer readable media) in a number of manners. Hard-wired circuitry or custom hardware may be used in place of, or in combination with, some or all of the software instructions that can implement the processes of various embodiments. Thus, various combinations of hardware and software may be used instead of software only.

Figure 3:
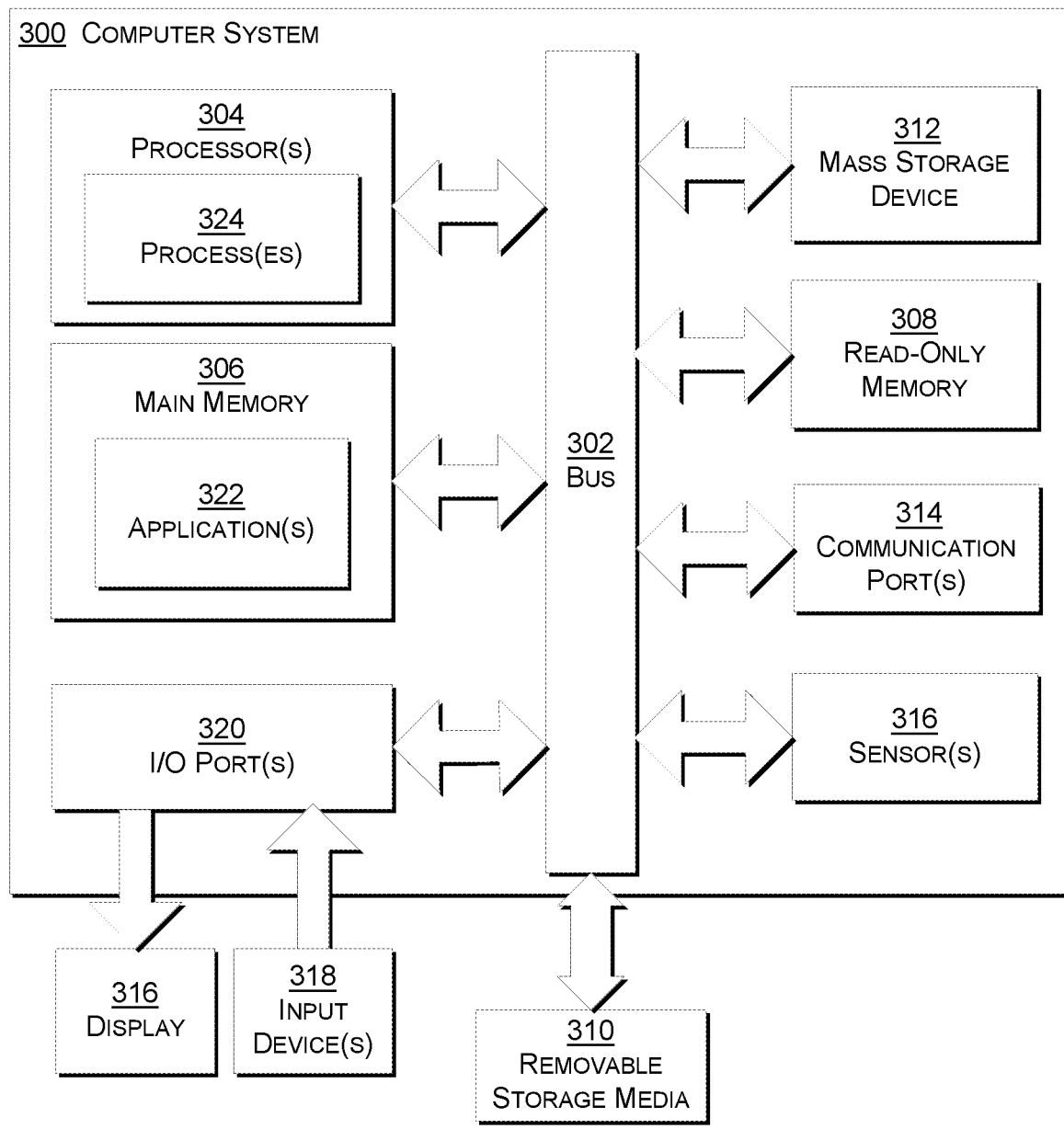

FIG. 3 is a schematic diagram of a computer system 300 upon which embodiments of the present disclosure may be implemented and carried out.

According to the present example, the computer system 300 includes a bus 302 (i.e., interconnect), one or more processors 304, one or more communications ports 314, a main memory 306, removable storage media 310, read-only memory 308, and a mass storage 312. Communication port(s) 314 may be connected to one or more networks by way of which the computer system 300 may receive and/or transmit data.

As used herein, a "processor" means one or more microprocessors, central processing units (CPUs), computing devices, microcontrollers, digital signal processors, or like devices or any combination thereof, regardless of their architecture. An apparatus that performs a process can include, e.g., a processor and those devices such as input devices and output devices that are appropriate to perform the process.

Processor(s) 304 can be (or include) any known processor, such as, but not limited to, an Intel® Itanium® or Itanium 2® processor(s), AMID® Opteron® or Athlon MP® processor(s), or Motorola® lines of processors, and the like. Communications port(s) 314 can be any of an RS-232 port for use with a modem based dial-up connection, a 10/100 Ethernet port, a Gigabit port using copper or fiber, or a USB port, and the like. Communications port(s) 314 may be chosen depending on a network such as a Local Area Network (LAN), a Wide Area Network (WAN), a CDN, or any network to which the computer system 300 connects. The computer system 300 may be in communication with peripheral devices (e.g., display screen 316, input device(s) 318) via Input/Output (I/O) port 320. Some or all of the peripheral devices may be integrated into the computer system 300, and the input device(s) 318 may be integrated into the display screen 316 (e.g., in the case of a touch screen).

Main memory 306 can be Random Access Memory (RAM), or any other dynamic storage device(s) commonly known in the art. Read-only memory 308 can be any static storage device(s) such as Programmable Read-Only Memory (PROM) chips for storing static information such as instructions for processor(s) 304. Mass storage 312 can be used to store information and instructions. For example, hard disks such as the Adaptec® family of Small Computer Serial Interface (SCSI) drives, an optical disc, an array of disks such as Redundant Array of Independent Disks (RAID), such as the Adaptec® family of RAID drives, or any other mass storage devices may be used.

Bus 302 communicatively couples processor(s) 304 with the other memory, storage and communications blocks. Bus 302 can be a PCI/PCI-X, SCSI, a Universal Serial Bus (USB) based system bus (or other) depending on the storage devices used, and the like. Removable storage media 310 can be any kind of external hard-drives, floppy drives, IOMEGA® Zip Drives, Compact Disc-Read Only Memory (CD-ROM), Compact Disc-Re-Writable (CD-RW), Digital Versatile Disk-Read Only Memory (DVD-ROM), etc.

Embodiments herein may be provided as one or more computer program products, which may include a machine-readable medium having stored thereon instructions, which may be used to program a computer (or other electronic devices) to perform a process. As used herein, the term "machine-readable medium" refers to any medium, a plurality of the same, or a combination of different media, which participate in providing data (e.g., instructions, data structures) which may be read by a computer, a processor or a like device. Such a medium may take many forms, including but not limited to, non-volatile media, volatile media, and transmission media. Non-volatile media include, for example, optical or magnetic disks and other persistent memory. Volatile media include dynamic random access memory, which typically constitutes the main memory of the computer. Transmission media include coaxial cables, copper wire and fiber optics, including the wires that comprise a system bus coupled to the processor. Transmission media may include or convey acoustic waves, light waves and electromagnetic emissions, such as those generated during radio frequency (RF) and infrared (IR) data communications.

The machine-readable medium may include, but is not limited to, floppy diskettes, optical discs, CD-ROMs, magneto-optical disks, ROMs, RAMs, erasable programmable read-only memories (EPROMs), electrically erasable programmable read-only memories (EEPROMs), magnetic or optical cards, flash memory, or other type of media/machine-readable medium suitable for storing electronic instructions. Moreover, embodiments herein may also be downloaded as a computer program product, wherein the program may be transferred from a remote computer to a requesting computer by way of data signals embodied in a carrier wave or other propagation medium via a communication link (e.g., modem or network connection).

Various forms of computer readable media may be involved in carrying data (e.g. sequences of instructions) to a processor. For example, data may be (i) delivered from RAM to a processor; (ii) carried over a wireless transmission medium; (iii) formatted and/or transmitted according to numerous formats, standards or protocols; and/or (iv) encrypted in any of a variety of ways well known in the art.

A computer-readable medium can store (in any appropriate format) those program elements that are appropriate to perform the methods.

As shown, main memory 306 is encoded with application(s) 322 that support(s) the functionality as discussed herein (an application 322 may be an application that provides some or all of the functionality of one or more of the mechanisms described herein). Application(s) 322 (and/or other resources as described herein) can be embodied as software code such as data and/or logic instructions (e.g., code stored in the memory or on another computer readable medium such as a disk) that supports processing functionality according to different embodiments described herein.

During operation of one embodiment, processor(s) 304 accesses main memory 306 via the use of bus 302 in order to launch, run, execute, interpret or otherwise perform the logic instructions of the application(s) 322. Execution of application(s) 322 produces processing functionality of the service(s) or mechanism(s) related to the application(s). In other words, the process(es) 324 represents one or more portions of the application(s) 322 performing within or upon the processor(s) 304 in the computer system 300.

It should be noted that, in addition to the process(es) 324 that carries(carry) out operations as discussed herein, other embodiments herein include the application 322 itself (i.e., the un-executed or non-performing logic instructions and/or data). The application 322 may be stored on a computer readable medium (e.g., a repository) such as a disk or in an optical medium. According to other embodiments, the application 322 can also be stored in a memory type system such as in firmware, read only memory (ROM), or, as in this example, as executable code within the main memory 306 (e.g., within Random Access Memory or RAM). For example, application 322 may also be stored in removable storage media 310, read-only memory 308, and/or mass storage device 312.

The application(s) 322 may correspond, at least in part, to one or more of the mechanisms 102 shown in FIG. 1. For example, each of the "Pattern" mechanism; the "count" mechanisms; the "offset count, bigger length" mechanism;

the "offset count, ignore length" mechanism; the iScore mechanism; the Signature mechanism; PhV mechanism; and the Position in Vector (PiV) mechanism may conveniently be implemented by one or more application(s) 322 that, when executed, run as corresponding processes 324.

Those skilled in the art will understand that the computer system 300 can include other processes and/or software and hardware components, such as an operating system that controls allocation and use of hardware resources.

Those skilled in the art will understand that the computer system 300 can include other processes and/or software and hardware components, such as an operating system that controls allocation and use of hardware resources.

As discussed herein, embodiments of the present invention include various steps or operations. A variety of these steps may be performed by hardware components or may be embodied in machine-executable instructions, which may be used to cause a general-purpose or special-purpose processor programmed with the instructions to perform the operations. Alternatively, the steps may be performed by a combination of hardware, software, and/or firmware. The term "module" refers to a self-contained functional component, which can include hardware, software, firmware or any combination thereof.

One of ordinary skill in the art will readily appreciate and understand, upon reading this description, that embodiments of an apparatus may include a computer/computing device operable to perform some (but not necessarily all) of the described process.

Embodiments of a computer-readable medium storing a program or data structure include a computer-readable medium storing a program that, when executed, can cause a processor to perform some (but not necessarily all) of the described process.

Where a process is described herein, those of skill in the art will appreciate that the process may operate without any user intervention. In another embodiment, the process includes some human intervention (e.g., a step is performed by or with the assistance of a human).

As used in this description, the term "portion" means some or all. So, for example, "A portion of X" may include some of "X" or all of "X". In the context of a sequence, the term "portion" means some or all of the sequence.

As used herein, including in the claims, the phrase "at least some" means "one or more," and includes the case of only one. Thus, e.g., the phrase "at least some ABCs" means "one or more ABCs", and includes the case of only one ABC.

As used herein, including in the claims, the phrase "based on" means "based in part on" or "based, at least in part, on," and is not exclusive. Thus, e.g., the phrase "based on factor X" means "based in part on factor X" or "based, at least in part, on factor X." Unless specifically stated by use of the word "only", the phrase "based on X" does not mean "based only on X."

As used herein, including in the claims, the phrase "using" means "using at least," and is not exclusive. Thus, e.g., the phrase "using X" means "using at least X." Unless specifically stated by use of the word "only", the phrase "using X" does not mean "using only X."

In general, as used herein, including in the claims, unless the word "only" is specifically used in a phrase, it should not be read into that phrase.

As used herein, including in the claims, the phrase "overlap" means "at least partially overlap." Unless specifically stated, "overlap" does not mean fully overlap. Thus, by way of non-limiting example, the sequence "ABCD" may be said to overlap the sequence "BCDE" and the sequence "ABCDE" and the sequence "DEFG".

As used herein, including in the claims, the phrase "distinct" means "at least partially distinct." Unless specifically stated, distinct does not mean fully distinct. Thus, e.g., the phrase, "X is distinct from Y" means that "X is at least partially distinct from Y," and does not mean that "X is fully distinct from Y." Thus, as used herein, including in the claims, the phrase "X is distinct from Y" means that X differs from Y in at least some way. It should be appreciated that two fully or partially overlapping sequences can be distinct. As a non-limiting example, the sequence "BCD" overlaps and is distinct from the sequence "ABCDE".

As used herein, including in the claims, a list may include only one item, and, unless otherwise stated, a list of multiple items need not be ordered in any particular manner. A list may include duplicate items. For example, as used herein, the phrase "a list of XYZs" may include one or more "XYZs".

It should be appreciated that the words "first", "second", "third," and so on, if used in the claims, are used to distinguish or identify, and not to show a serial or numerical limitation. Similarly, the use of letter or numerical labels (such as "(a)", "(b)", and the like) are used to help distinguish and/or identify, and not to show any serial or numerical limitation or ordering.

No ordering is implied by any of the labeled boxes in any of the flow diagrams unless specifically shown and stated. When disconnected boxes are shown in a diagram the activities associated with those boxes may be performed in any order, including fully or partially in parallel.

While the invention has been described in connection with and with respect to protein, DNA, and RNA molecules, those of ordinary skill in the art will realize and appreciate, upon reading this description, that these techniques may be applied to other molecules, including molecules in a genome (including non-coding molecules).

While the invention has been described in connection with what is presently considered to be the most practical and preferred embodiments, it is to be understood that the invention is not to be limited to the disclosed embodiment, but on the contrary, is intended to cover various modifications and equivalent arrangements included within the spirit and scope of the appended claims.

Appendix I (Source Code)

Exemplary source code (in the Ruby programming language) is shown below:

```ruby
#Generate offset counts & iscore report
#Function 1: Scan sequences and generate offsetcounts & iScore
#input example:
#[{"transcript_id"=>"ENST00000377313", "Direction" => "F",
"offset" => 0, "sequence"=>"GATTGAT", "protein_hash_value" =>
10016473972116439183}, {"transcript_id"=>"ENST00000377313",
"Direction" => "F", "offset" => 1, "sequence"=>"GATTGATCC",
"protein_hash_value" => 10016473972116439183},
{"transcript_id"=>"ENST00000377313", "Direction" => "F",
"offset" => 2, "sequence"=>"GATTG", "protein_hash_value" =>
12865572994853230352}, {"transcript_id"=>"ENST00000377313",
"Direction" => "Fr", "offset" => 3,
"sequence"=>"TTTTTTTTTTTTTT", "protein_hash_value" =>
9662452273227638168}, {"transcript_id"=>"ENST00000394374",
"Direction" => "F", "offset" => 0, "sequence"=>"GATTGATCC",
"protein_hash_value" => 9662452273227638168}]
# run Iscore.test_iscore to run an example
#Function 2: Generate iscore report
#input example:
#[{"transcript_id"=>"ENST00000377313", "Direction" => "F",
"offset" => 0, "sequence"=>"GATTGAT", "protein_hash_value" =>
10016473972116439183}, {"transcript_id"=>"ENST00000377313",
"Direction" => "F", "offset" => 1, "sequence"=>"GATTGATCC",
"protein_hash_value" => 10016473972116439183},
{"transcript_id"=>"ENST00000377313", "Direction" => "F",
"offset" => 2, "sequence"=>"GATTG", "protein_hash_value" =>
12865572994853230352}, {"transcript_id"=>"ENST00000377313",
"Direction" => "Fr", "offset" => 3,
"sequence"=>"TTTTTTTTTTTTTT", "protein_hash_value" =>
9662452273227638168}, {"transcript_id"=>"ENST00000394374",
"Direction" => "F", "offset" => 0, "sequence"=>"GATTGATCC",
"protein_hash_value" => 9662452273227638168}]
```

```
# run Iscore.test_iscore_report to run an example

#Function 3: generate a particular offset iscore
#Iscore.test_iscore_specific_offset("ENST00000600453",130, "F")
#Iscore.test_iscore_specific_offset("ENST00000597198",154, "F")

#Function 4: another example of iscore report
#Iscore.test_iscore_report_specific_offset
class Iscore
  require 'json' def self.generate_offset_counts(sequences_array, offset = nil, direction = "F")
    icount = 0
    sequences_array.each do |value_hash|
      value_hash["offset_counts_same_transcript_bigger_length"] = 0
      value_hash["offset_counts_same_transcript_ignore_length"] = 0
      value_hash["offset_counts_diff_transcript_ignore_length"] = 0
      value_hash["offset_counts_diff_transcript_bigger_length"] = 0
      next if !offset.nil? && (offset != value_hash["offset"] || direction !=  value_hash["Direction"])
      sequences_array.each do |compare_hash|
        bigger_count = 0
        smaller_count = 0
        src_length = value_hash["sequence"].length
        compare_length = compare_hash["sequence"].length
        if src_length <= compare_length && compare_hash["sequence"].include?(value_hash["sequence"])
          bigger_count = 1
        end
```

```
            if src_length > compare_length &&
value_hash["sequence"].include?(compare_hash["sequence"])
                smaller_count = 1
              end
if value_hash["transcript_id"] == compare_hash["transcript_id"]
              if bigger_count == 1 value_hash["offset_counts_same_transcript_bigger_length"] += 1 value_hash["offset_counts_same_transcript_ignore_length"] += 1
              end
              if smaller_count == 1 value_hash["offset_counts_same_transcript_ignore_length"] += 1
              end
            else
              if bigger_count == 1 value_hash["offset_counts_diff_transcript_bigger_length"] += 1 value_hash["offset_counts_diff_transcript_ignore_length"] += 1
              end
              if smaller_count == 1 value_hash["offset_counts_diff_transcript_ignore_length"] += 1
              end
            end
          end
        end
        icount += 1
        puts "Process: #{icount}"
      end
      return sequences_array
    end
def self.calculate_iscore(sequences_array)
      puts "calculate_iscore"
      sequences_array.each do |value_hash|
```

```ruby
      value_hash["iscore"] =
(value_hash["offset_counts_same_transcript_ignore_length"] -
value_hash["offset_counts_same_transcript_bigger_length"]) * 1.0
/ value_hash["sequence"].length
    end
    return sequences_array
  end def self.transfer_to_report_input_hash(sequence_array)
    ret_hash = Hash.new
    sequence_array.each do |sequence_hash|
      key = sequence_hash["Direction"] +
sequence_hash["offset"].to_s
      ret_hash[key] = Hash.new if !ret_hash.has_key?(key)
      ret_hash[key][sequence_hash["transcript_id"]] = {"p" =>
sequence_hash["protein_hash_value"], "i" =>
sequence_hash["iscore"]}
    end
    return ret_hash
  end

#Function 1: generate iScore
  def self.test_iscore
    sequences_array = [{"transcript_id"=>"ENST00000377313",
"Direction" => "F", "offset" => 0, "sequence"=>"GATTGAT",
"protein_hash_value" => 10016473972116439183},
{"transcript_id"=>"ENST00000377313", "Direction" => "F",
"offset" => 1, "sequence"=>"GATTGATCC", "protein_hash_value" =>
10016473972116439183}, {"transcript_id"=>"ENST00000377313",
"Direction" => "F", "offset" => 2, "sequence"=>"GATTG",
"protein_hash_value" => 12865572994853230352},
{"transcript_id"=>"ENST00000377313", "Direction" => "Fr",
"offset" => 3, "sequence"=>"TTTTTTTTTTTTTT",
"protein_hash_value" => 9662452273227638168},
{"transcript_id"=>"ENST00000394374", "Direction" => "F",
```

```
"offset" => 0, "sequence"=>"GATTGATCC", "protein_hash_value" =>
9662452273227638168}]
    sequences_array = generate_offset_counts(sequences_array)
    sequences_array = calculate_iscore(sequences_array)
    puts sequences_array.to_json
    return sequences_array
  end

#Function 2: generate iScore reports
  def self.test_iscore_report
    input_hashes = transfer_to_report_input_hash(test_iscore)
    input_hashes.each do |key, input_hash|
      next if input_hash.size == 1
      puts Report.generate(input_hash).to_json
    end
  end

#Function 3: generate iScore for specific offset
  def
self.test_iscore_specific_offset(transcript_stable_id,offset,
direction = "F")
    sequences_array = input_data(transcript_stable_id)
    sequences_array = generate_offset_counts(sequences_array,
offset)
    sequences_array = calculate_iscore(sequences_array)
    sequences_array.each do |seq_hash|
      puts seq_hash if seq_hash["offset"] == offset && direction
==   seq_hash["Direction"]
    end
    return nil;
  end def self.input_data(stable_id)
  puts "input_data"
    t_array = Array.new
```

```
    File.foreach("resources/#{stable_id}.csv").with_index do
|line, line_num|
        #puts "#{line_num}: #{line}"
        t_input = line.gsub(/\r|\t|\n/,"").split(",")
        raise "Data format error!" if t_input.size != 5
        t_hash = Hash.new
        t_hash["transcript_id"] = t_input[0]
        t_hash["Direction"] = t_input[1]
        t_hash["offset"] = t_input[2].to_i
        t_hash["protein_hash_value"] = t_input[3].to_i
        t_hash["sequence"] = t_input[4]
        t_array.push t_hash
    end
    return t_array
  end

#Function 4: generate iScore reprot for specific offset
  def self.test_iscore_report_specific_offset
    input_hash = {"ENST00000596756"=>{"p"=>4006617391866799131,
"i"=>3.6666666666666665},
"ENST00000597198"=>{"p"=>12271691713048959439,
"i"=>3.6666666666666665},
"ENST00000309877"=>{"p"=>12271691713048959439,
"i"=>3.611111111111111},
"ENST00000600911"=>{"p"=>5168434887446584552,
"i"=>3.611111111111111},
"ENST00000597636"=>{"p"=>9314657173126866352,
"i"=>3.611111111111111},
"ENST00000442265"=>{"p"=>13186677374619181588,
"i"=>3.611111111111111},
"ENST00000377135"=>{"p"=>14380345047581822947,
"i"=>3.611111111111111},
"ENST00000593337"=>{"p"=>10922829938332626334,
"i"=>3.611111111111111},
"ENST00000601809"=>{"p"=>13988773081312178186,
"i"=>3.611111111111111},
```

```
"ENST00000601373"=>{"p"=>10752208690176199972,
"i"=>3.611111111111111},
"ENST00000596765"=>{"p"=>4242541338062981510,
"i"=>3.611111111111111},
"ENST00000600022"=>{"p"=>4242541338062981510,
"i"=>3.611111111111111},
"ENST00000599144"=>{"p"=>9284278690327170613,
"i"=>3.611111111111111},
"ENST00000598808"=>{"p"=>9284278690327170613,
"i"=>3.611111111111111},
"ENST00000593922"=>{"p"=>9284278690327170613,
"i"=>3.611111111111111},
"ENST00000377139"=>{"p"=>12271691713048959439,
"i"=>3.611111111111111},
"ENST00000599223"=>{"p"=>14380345047581822947,
"i"=>3.611111111111111},
"ENST00000596822"=>{"p"=>14742079273191910198,
"i"=>3.611111111111111},
"ENST00000595034"=>{"p"=>14904930809086793406,
"i"=>3.611111111111111},
"ENST00000601291"=>{"p"=>15016766153870036082,
"i"=>3.611111111111111},
"ENST00000600453"=>{"p"=>12599430326588101984,
"i"=>4.055555555555555},
"ENST00000596788"=>{"p"=>1939525357298296176,
"i"=>3.7222222222222223},
"ENST00000593818"=>{"p"=>4343270347374302829,
"i"=>3.611111111111111},
"ENST00000598108"=>{"p"=>12020088722410334026,
"i"=>3.611111111111111}}
    puts Report.generate(input_hash).to_json
  end
end puts "Testing iscore"
```

```
Iscore.test_iscore_specific_offset("ENST00000600453",130, "F")

#Generate POP, GR and CR

class Report def self.generate(input_hash, transcripts_count = nil)

step 1: Generate protein rank/sort position
    sort_by_hash_value(input_hash, "p")

#step 2: Generate intron rank/sort position
    sort_by_hash_value(input_hash, "i")

#step3: Reorder
    #step3.1 group
    regroup_hash = regroup(input_hash)

#step3.2 reorder the group
    reorder(regroup_hash, input_hash)

#calculate POP, GR, CR
    return calculate(input_hash, transcripts_count)
  end def self.calculate(input_hash, transcripts_count = nil)
    transcripts_count = input_hash.size if transcripts_count.nil?
    sorted_tmp = input_hash.sort_by { |stable_id, hash_values| hash_values["intron_order_position"] }
    pop = 0
    total_gene_rank = 0
    sorted_tmp.each_with_index do |transcript, i_index|
      values = transcript[1]
      values["gene_rank"] = (values["p_ranking_position"] - values["i_ranking_position"]).abs
```

```ruby
      values["paired"] = false
      total_gene_rank += values["gene_rank"]
      if i_index == 0
        values["paired"] = true if values["p_ranking_position"] == sorted_tmp[i_index + 1][1]["p_ranking_position"] || values["intron_order_position"] == values["p_ranking_position"]
      elsif i_index == (sorted_tmp.size - 1)
        values["paired"] = true if values["p_ranking_position"] == sorted_tmp[i_index - 1][1]["p_ranking_position"] || values["intron_order_position"] == values["p_ranking_position"]
      else
        values["paired"] = true if values["p_ranking_position"] == sorted_tmp[i_index + 1][1]["p_ranking_position"] || values["p_ranking_position"] == sorted_tmp[i_index - 1][1]["p_ranking_position"] || values["intron_order_position"] == values["p_ranking_position"]
      end
      pop += 1 if values["paired"]
    end if input_hash.blank?
      order_percentage = nil
      gene_rank = nil
      combine_score =  nil
    else
      order_percentage = pop * 1.0 / transcripts_count
      gene_rank = total_gene_rank * 1.0 / input_hash.size
      combine_score =  gene_rank - order_percentage
    end print_hash(input_hash)
    return {"POP" => order_percentage, "GR" => gene_rank, "CR" => combine_score} end
```

```
  def self.print_hash(input_hash)
    sorted_tmp = input_hash.sort_by { |stable_id, hash_values|
hash_values["intron_order_position"] }
    puts "NO.,   Transcript,    Intron Value/iScore, Intron
Order, Protein Order, Protein Value, Gene Rank Intron Order,
Gene Rank"
    sorted_tmp.each_with_index do |transcript, index|
      puts "#{transcript[1]["paired"] ? "*" : ""}[#{index + 1}]
#{transcript[0]}, #{transcript[1]["i"]},
#{transcript[1]["intron_order_position"]},
#{transcript[1]["p_ranking_position"]}, #{transcript[1]["p"]},
#{transcript[1]["i_ranking_position"]},
#{transcript[1]["gene_rank"]} "
    end
  end def self.reorder(regroup_hash, input_hash)
    # generate a temp hash which will be used later to determine
bottom
    grouped_p_ranking_positions_hash = Hash.new
    regroup_hash.each_pair do |group_number, transcripts|
      grouped_p_ranking_positions_hash[group_number] = Array.new
if !grouped_p_ranking_positions_hash.has_key? group_number
      transcripts.each_pair do |stable_id, p_ranking_position|
        grouped_p_ranking_positions_hash[group_number].push
p_ranking_position
      end
    end group_index = 0
    previous_buttom = nil
    group_numbers = regroup_hash.keys.sort
    group_numbers.each do |group_number|
      transcripts = regroup_hash[group_number]
      handled = Array.new
      top_index = 0
```

```
      # decide top
      if group_number > 0 # skip the first group
         tmp_index = 0
         transcripts.each_pair do |stable_id, p_ranking_position|
            if p_ranking_position == previous_buttom
               tmp_index += 1
               top_index += 1
               input_hash[stable_id]["intron_order_position"] =
group_index + tmp_index
               handled.push stable_id
            end
         end
      end decide bottom
      if group_number < group_numbers.size #skip the last group
         #determin the bottom
         bottom_cadidates = Array.new
         temp_hash = Hash.new remove pared to top and already paired ones
         transcripts.each_pair do   |stable_id,
p_ranking_position|
            next if handled.include? stable_id
            if temp_hash.has_key? p_ranking_position
               temp_hash[p_ranking_position] += 1
            else
               temp_hash[p_ranking_position] = 1
            end
         end generate bottom candidates
         temp_hash.each_pair do |p_ranking_position, count|
            bottom_cadidates.push p_ranking_position if (count ==
1) && (grouped_p_ranking_positions_hash[group_number +
1].include? p_ranking_position)
```

```
          end if bottom_cadidates.size > 1
         bottom = determine_bot(bottom_cadidates, group_number
+ 1, grouped_p_ranking_positions_hash)
      elsif bottom_cadidates.size == 1
         bottom = bottom_cadidates.first
      end if !bottom.nil?
         tmp_index = 0
         transcripts.each_pair do |stable_id,
p_ranking_position|
            if p_ranking_position == bottom &&
!(handled.include? stable_id)
               input_hash[stable_id]["intron_order_position"] =
group_index + transcripts.size - tmp_index
               tmp_index += 1
               handled.push stable_id
            end
          end
        end
      end sort middle
      tt_hash = Hash.new
      transcripts.each_pair do |stable_id, p_ranking_position|
         next if (handled.include? stable_id)
         tt_hash[stable_id] = p_ranking_position
      end if tt_hash.size > 0
         sorted_tt_hash = tt_hash.sort_by { |stable_id,
p_ranking_position| p_ranking_position }
```

```
sorted_tt_hash.each_with_index do |(stable_id,
p_ranking_position), ii|
          input_hash[stable_id]["intron_order_position"] =
group_index + top_index + ii + 1
          bottom = p_ranking_position if ii ==
(sorted_tt_hash.size - 1) && bottom.nil?
        end end
group_index += transcripts.size
      previous_buttom = bottom if !bottom.nil?# reset bottom,
bottom is nil only all pushed to top
    end
  end def self.determine_bot(candidates, index, array)
    return nil if index > array.size # max out
    candidates.sort.each do |c|
      return c if !array[index].include?(c)
    end
    return determine_bot(candidates, index + 1, array)
  end def self.sort_by_hash_value(input_hash, hash_value_type)
    sorted_tmp = input_hash.sort_by { |stable_id, hash_values|
hash_values[hash_value_type] }
    prev_hash_value = nil
    current_paired_position = 1
    current_rank_posistion = 1
    sorted_tmp.each_with_index do |a, index| if index > 0 && a[1][hash_value_type] != prev_hash_value
        current_paired_position += 1
        current_rank_posistion = index + 1
      end
```

```
      input_hash[a.first][hash_value_type + "_paired_position"]
= current_paired_position
      input_hash[a.first][hash_value_type + "_ranking_position"]
= current_rank_posistion
      prev_hash_value = a[1][hash_value_type]
    end
    return  input_hash
  end
def self.regroup(hash_value)
    group_hash = Hash.new
    hash_value.each_pair do |stable_id, values|
      group_hash[values["i_paired_position"]] = {stable_id =>
values["p_ranking_position"]} if !group_hash.has_key?
values["i_paired_position"]
      group_hash[values["i_paired_position"]][stable_id] =
values["p_ranking_position"]
    end
    return group_hash
  end
def self.test
    input = {"ENST00000377313"=>{"p"=>10016473972116439183,
"i"=>1676130665177741313},
"ENST00000394374"=>{"p"=>10016473972116439183,
"i"=>2503961881512634917},
"ENST00000394376"=>{"p"=>10016473972116439183,
"i"=>5164633206682038560},
"ENST00000424912"=>{"p"=>12865572994853230352,
"i"=>5164633206682038560},
"ENST00000429702"=>{"p"=>12865572994853230352,
"i"=>5819545816596913902},
"ENST00000337652"=>{"p"=>10016473972116439183,
"i"=>5819545816596913902},
"ENST00000443283"=>{"p"=>10016473972116439183,
"i"=>7189214929071588867},
"ENST00000440873"=>{"p"=>9662452273227638168,
"i"=>9351644970681852145},
```

```
"ENST00000377321"=>{"p"=>10854016887269896695,
"i"=>9351644970681852145},
"ENST00000377316"=>{"p"=>10702732961978641103,
"i"=>9534311961692397952},
```

```
"ENST00000377321"=>{"p"=>10854016887269896695,
"i"=>9351644970681852145},
"ENST00000377316"=>{"p"=>10702732961978641103,
"i"=>9534311961692397952},
"ENST00000377326"=>{"p"=>13888077090689236035,
"i"=>9534311961692397952},
"ENST00000315422"=>{"p"=>13888077090689236035,
"i"=>12292542568658633110},
"ENST00000312049"=>{"p"=>13888077090689236035,
"i"=>15081914161581960811},
"ENST00000450708"=>{"p"=>6743057925785323865,
"i"=>16379423582671150862},
"ENST00000413626"=>{"p"=>15724440847510920542,
"i"=>18300401426631122607}}
    puts generate(input)
  end
end
```

We claim:

1. A computer-implemented method, implemented by hardware in combination with software, said method comprising, for a particular gene having multiple protein-coding transcripts, each of said protein-coding transcripts comprising a corresponding at least one intron portion, and each of said protein-coding transcripts encoding a corresponding protein, (A) determining a sequence of said multiple protein-coding transcripts;

(B) determining multiple scores, each of said scores corresponding to or based on the at least one intron portion of a corresponding one of said multiple protein-coding transcripts;

(C) determining multiple protein signatures corresponding to proteins encoded by the multiple protein-coding transcripts;

(D) determining at least one ordering of said sequence of said multiple protein-coding transcripts, wherein said determining is based on said multiple scores and said multiple protein signatures;

(E) selecting a subset of said protein-coding transcripts, said selecting being based on said at least one ordering of said sequence; and (F) using said subset of said protein-coding transcripts to determine or confirm at least one aspect of a genetic function of at least some of said protein-coding transcripts, wherein the score for a particular nucleotide sequence is based on a count of sub-sequence recurrence or inter-inclusiveness based on a one-nucleotide advance in said particular nucleotide sequence.

2. The method of claim 1, wherein the score for a particular nucleotide sequence corresponds to an iScore of the particular nucleotide sequence.

3. The method of claim 1, wherein said determining in (D) comprises sorting said sequence of said multiple protein-coding transcripts based on one or more of: (i) said scores, and (ii) said protein signatures.

4. The method of claim 1, wherein said selecting in (E) is based on at least one position of said protein-coding transcripts in said at least one ordering of said sequence.

5. The method of claim 1,
wherein a particular protein coding transcript comprises a particular one or more intron portions, and wherein a score for the particular protein coding transcript is determined in (B) based on a first computational function of the particular one or more intron portions.

6. The method of claim 5, wherein the first computational function comprises a first hash function.

7. The method of claim 1, wherein a particular protein coding transcript encodes a particular protein, and wherein a particular protein signature is determined in (C) based on a second computational function of the particular protein.

8. The method of claim 1, wherein said determining a sequence in (A) comprises forming said sequence in a database.

9. The method of claim 8, further comprising:
forming, in said database, one or more associations between said protein-coding transcripts, said scores, and said, protein signatures.

10. The method of claim 9, wherein said selecting in (E) uses said at least one ordering using said one or more associations.

11. The method of claim 10, wherein said
using in (F) also uses other associations in said database between other signature values of other character strings to determine or confirm said at least one aspect of a genetic function of said particular nucleotide sequence.

12. The method of claim 9, further comprising:
forming, in said database, an association between at least some of said subset of said protein-coding transcripts and said genetic function.

13. A non-transitory computer-readable medium storing one or more programs, which, when executed, cause one or more processors to, at least perform the method of claim 1.

14. A computer-implemented method, implemented by hardware in combination with software, said method comprising, for a particular gene having multiple protein-coding transcripts, each of said protein-coding transcripts comprising a corresponding at least one intron portion, and each of said protein-coding transcripts encoding a corresponding protein, (A) determining a sequence of said multiple protein-coding transcripts;

(B) determining multiple scores, each of said scores corresponding to or based on the at least one intron portion of a corresponding one of said multiple protein-coding transcripts;

(C) determining multiple protein signatures corresponding to proteins encoded by the multiple protein-coding transcripts;

(D) determining at least one ordering of said sequence of said multiple protein-coding transcripts, wherein said determining is based on said multiple scores and said multiple protein signatures;

(E) selecting a subset of said protein-coding transcripts, said selecting being based on said at least one ordering of said sequence; and (F) using said subset of said protein-coding transcripts to determine or confirm at least one aspect of a genetic function of at least some of said protein-coding transcripts, wherein a particular protein coding transcript comprises a particular one or more intron portions, and wherein a score for the particular protein coding transcript is determined in (B) based on a first computational function of the particular one or more intron portions.

15. The method of claim 14, wherein the first computational function comprises a first hash function.

16. The method of claim 14, wherein a particular protein coding transcript encodes a particular protein, and wherein a particular protein signature is determined in (C) based on a second computational function of the particular protein.

17. The method of claim 14, wherein said determining a sequence in (A) comprises forming said sequence in a database.

18. The method of claim 17, further comprising:
forming, in said database, one or more associations between said protein-coding transcripts, said scores, and said, protein signatures.

19. The method of claim 18, wherein said selecting in (E) uses said at least one ordering using said one or more associations.

20. The method of claim 19, wherein said
using in (F) also uses other associations in said database between other signature values of other character strings to determine or confirm said at least one aspect of a genetic function of a particular nucleic acid sequence.

21. The method of claim 18, further comprising:
forming, in said database, an association between at least some of said subset of said protein-coding transcripts and said genetic function.

22. The method of claim 14, wherein the score for a particular nucleotide sequence is based on a count of sub-sequence recurrence or inter-inclusiveness based on a one-nucleotide advance in said particular nucleotide sequence.

23. The method of claim 14, wherein the score for a particular nucleotide sequence corresponds to an iScore of the particular nucleotide sequence.

24. The method of claim 14, wherein said determining in (D) comprises sorting said sequence of said multiple protein-coding transcripts based on one or more of: (i) said scores, and (ii) said protein signatures.

25. The method of claim 14, wherein said selecting in (E) is based on at least one position of said protein-coding transcripts in said at least one ordering of said sequence.

* * * * *

SEQUENCE LISTING

<160> NUMBER OF SEQ ID NOS: 146

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gtgggcccag ac                                                            12

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gtgggcccag                                                               10

<210> SEQ ID NO 3
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gggcccagac                                                               10

<210> SEQ ID NO 4
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tgggcccaga c                                                             11

<210> SEQ ID NO 5
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gtgggcccag ac                                                            12

<210> SEQ ID NO 6
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gtgggcccag ac                                                            12

<210> SEQ ID NO 7
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gtgggcccag                                                           10

<210> SEQ ID NO 8
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tgggcccaga                                                           10

<210> SEQ ID NO 9
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gtgggcccag a                                                         11

<210> SEQ ID NO 10
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gggcccagac                                                           10

<210> SEQ ID NO 11
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tgggcccaga c                                                         11

<210> SEQ ID NO 12
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gtgggcccag ac                                                        12

<210> SEQ ID NO 13
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gtgggcccag ac                                                             12

<210> SEQ ID NO 14
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gtgggcccag                                                                10

<210> SEQ ID NO 15
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tgggcccaga                                                                10

<210> SEQ ID NO 16
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gtgggcccag a                                                              11

<210> SEQ ID NO 17
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gggcccagac                                                                10

<210> SEQ ID NO 18
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tgggcccaga c                                                              11

```
<210> SEQ ID NO 19
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gtgggcccag ac                                                           12

<210> SEQ ID NO 20
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gtgggcccag                                                              10

<210> SEQ ID NO 21
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gtgggcccag a                                                            11

<210> SEQ ID NO 22
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gtgggcccag ac                                                           12

<210> SEQ ID NO 23
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gtgggcccag                                                              10

<210> SEQ ID NO 24
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
tgggcccaga                                                              10

<210> SEQ ID NO 25
```

-continued

```
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gtgggcccag a                                                            11

<210> SEQ ID NO 26
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gggcccagac                                                              10

<210> SEQ ID NO 27
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
tgggcccaga c                                                            11

<210> SEQ ID NO 28
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gtgggcccag ac                                                           12

<210> SEQ ID NO 29
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gtgggcccag                                                              10

<210> SEQ ID NO 30
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gtgggcccag a                                                            11

<210> SEQ ID NO 31
<211> LENGTH: 12
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gtgggcccag ac                                                              12

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gtgcccccgg actacatttt                                                      20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gtgcccccgg actacatttt                                                      20

<210> SEQ ID NO 34
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
gtgcccccgg                                                                 10

<210> SEQ ID NO 35
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
tgcccccgga                                                                 10

<210> SEQ ID NO 36
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gtgcccccgg a                                                               11

<210> SEQ ID NO 37
<211> LENGTH: 10
<212> TYPE: DNA
```

-continued

<213> ORGANISM: Artificial Sequence
<220> FEATURE:
<223> OTHER INFORMATION: Description of Artificial Sequence: Synthetic
      oligonucleotide

<400> SEQUENCE: 37
gcccccggac                                                                10

<210> SEQ ID NO 38
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
tgcccccgga c                                                              11

<210> SEQ ID NO 39
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gtgcccccgg ac                                                             12

<210> SEQ ID NO 40
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
cccccggact                                                                10

<210> SEQ ID NO 41
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
gcccccggac t                                                              11

<210> SEQ ID NO 42
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
tgcccccgga ct                                                             12

<210> SEQ ID NO 43
<211> LENGTH: 13
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 43 gtgccccgg act                                                          13

<210> SEQ ID NO 44
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
ccccggacta                                                             10

<210> SEQ ID NO 45
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
cccccggact a                                                           11

<210> SEQ ID NO 46
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gcccccggac ta                                                          12

<210> SEQ ID NO 47
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
tgcccccgga cta                                                         13

<210> SEQ ID NO 48
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gtgcccccgg acta                                                        14

<210> SEQ ID NO 49
<211> LENGTH: 10
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 49
cccggactac                                                              10

<210> SEQ ID NO 50
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
ccccggacta c                                                            11

<210> SEQ ID NO 51
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
cccccggact ac                                                           12

<210> SEQ ID NO 52
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
gcccccggac tac                                                          13

<210> SEQ ID NO 53
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
tgcccccgga ctac                                                         14

<210> SEQ ID NO 54
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
gtgcccccgg actac                                                        15

<210> SEQ ID NO 55
<211> LENGTH: 10
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 55
ccggactaca                                                                 10

<210> SEQ ID NO 56
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
cccggactac a                                                               11

<210> SEQ ID NO 57
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
ccccggacta ca                                                              12

<210> SEQ ID NO 58
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
cccccggact aca                                                             13

<210> SEQ ID NO 59
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
gcccccggac taca                                                            14

<210> SEQ ID NO 60
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
tgcccccgga ctaca                                                           15

<210> SEQ ID NO 61
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
gtgcccccgg actaca                                                  16

<210> SEQ ID NO 62
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
cggactacat                                                         10

<210> SEQ ID NO 63
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
ccggactaca t                                                       11

<210> SEQ ID NO 64
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
cccggactac at                                                      12

<210> SEQ ID NO 65
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
ccccggacta cat                                                     13

<210> SEQ ID NO 66
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
cccccggact acat                                                    14

<210> SEQ ID NO 67
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 67
gcccccggac tacat                                                    15

<210> SEQ ID NO 68
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
tgcccccgga ctacat                                                   16

<210> SEQ ID NO 69
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
gtgcccccgg actacat                                                  17

<210> SEQ ID NO 70
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
ggactacatt                                                          10

<210> SEQ ID NO 71
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
cggactacat t                                                        11

<210> SEQ ID NO 72
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
ccggactaca tt                                                       12

<210> SEQ ID NO 73
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
```
cccggactac att                                                          13

<210> SEQ ID NO 74
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
ccccggacta catt                                                         14

<210> SEQ ID NO 75
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
cccccggact acatt                                                        15

<210> SEQ ID NO 76
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
gcccccggac tacatt                                                       16

<210> SEQ ID NO 77
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
tgcccccgga ctacatt                                                      17

<210> SEQ ID NO 78
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
gtgcccccgg actacatt                                                     18

<210> SEQ ID NO 79
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
gactacattt                                                              10

<210> SEQ ID NO 80
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
ggactacatt t                                                            11

<210> SEQ ID NO 81
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
cggactacat tt                                                           12

<210> SEQ ID NO 82
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
ccggactaca ttt                                                          13

<210> SEQ ID NO 83
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
cccggactac attt                                                         14

<210> SEQ ID NO 84
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
ccccggacta cattt                                                        15

<210> SEQ ID NO 85
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
cccccggact acattt                                                       16

```
<210> SEQ ID NO 86
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
gcccccggac tacattt                                                  17

<210> SEQ ID NO 87
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87 tgccccgga ctacattt                                                  18

<210> SEQ ID NO 88
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88 gtgccccgg actacattt                                                 19

<210> SEQ ID NO 89
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
actacatttt                                                          10

<210> SEQ ID NO 90
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
gactacattt t                                                        11

<210> SEQ ID NO 91
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
ggactacatt tt                                                       12
```

```
<210> SEQ ID NO 92
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
cggactacat ttt                                                          13

<210> SEQ ID NO 93
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
ccggactaca tttt                                                         14

<210> SEQ ID NO 94
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
cccggactac atttt                                                        15

<210> SEQ ID NO 95
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
ccccggacta catttt                                                       16

<210> SEQ ID NO 96
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
cccccggact acatttt                                                      17

<210> SEQ ID NO 97
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
gcccccggac tacatttt                                                     18
```

```
<210> SEQ ID NO 98
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
tgcccccgga ctacatttt                                                 19

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
gtgcccccgg actacatttt                                                20

<210> SEQ ID NO 100
<211> LENGTH: 18
<212> TYPE: DNA
<213> ORGANISM: Homo sapiens

<400> SEQUENCE: 100
gcacagtcgt agagaggg                                                  18

<210> SEQ ID NO 101
<211> LENGTH: 18
<212> TYPE: DNA
<213> ORGANISM: Homo sapiens

<400> SEQUENCE: 101
gggcacgctt cctgcctg                                                  18

<210> SEQ ID NO 102
<211> LENGTH: 18
<212> TYPE: DNA
<213> ORGANISM: Homo sapiens

<400> SEQUENCE: 102
ccagctaaag cggctgaa                                                  18

<210> SEQ ID NO 103
<211> LENGTH: 18
<212> TYPE: DNA
<213> ORGANISM: Homo sapiens

<400> SEQUENCE: 103
cccacttctt caaaaccc                                                  18

<210> SEQ ID NO 104
<211> LENGTH: 18
<212> TYPE: DNA
<213> ORGANISM: Homo sapiens

<400> SEQUENCE: 104
aggactctcc ttggggtt                                                  18

<210> SEQ ID NO 105
<211> LENGTH: 18
<212> TYPE: DNA
```

```
<213> ORGANISM: Homo sapiens

<400> SEQUENCE: 105
ccctccatgg tttacaga                                                 18

<210> SEQ ID NO 106
<211> LENGTH: 18
<212> TYPE: DNA
<213> ORGANISM: Homo sapiens

<400> SEQUENCE: 106
ccagctaaag cggctgaa                                                 18

<210> SEQ ID NO 107
<211> LENGTH: 18
<212> TYPE: DNA
<213> ORGANISM: Homo sapiens

<400> SEQUENCE: 107
ggggtttggg ggcttgac                                                 18

<210> SEQ ID NO 108
<211> LENGTH: 18
<212> TYPE: DNA
<213> ORGANISM: Homo sapiens

<400> SEQUENCE: 108
gagctgtgcg tgtgtcgg                                                 18

<210> SEQ ID NO 109
<211> LENGTH: 18
<212> TYPE: DNA
<213> ORGANISM: Homo sapiens

<400> SEQUENCE: 109
gaccctaggg gcgggact                                                 18

<210> SEQ ID NO 110
<211> LENGTH: 18
<212> TYPE: DNA
<213> ORGANISM: Homo sapiens

<400> SEQUENCE: 110
gggcacgctt cctgcctg                                                 18

<210> SEQ ID NO 111
<211> LENGTH: 18
<212> TYPE: DNA
<213> ORGANISM: Homo sapiens

<400> SEQUENCE: 111
gaccctaggg gcgggact                                                 18

<210> SEQ ID NO 112
<211> LENGTH: 18
<212> TYPE: DNA
<213> ORGANISM: Homo sapiens

<400> SEQUENCE: 112
cccacttctt caaaaccc                                                 18

<210> SEQ ID NO 113
<211> LENGTH: 18
```

<212> TYPE: DNA
<213> ORGANISM: Homo sapiens

<400> SEQUENCE: 113
ggggtttggg ggcttgac                                                18

<210> SEQ ID NO 114
<211> LENGTH: 18
<212> TYPE: DNA
<213> ORGANISM: Homo sapiens

<400> SEQUENCE: 114
gagctgtgcg tgtgtcgg                                                18

<210> SEQ ID NO 115
<211> LENGTH: 105
<212> TYPE: DNA
<213> ORGANISM: Homo sapiens

<400> SEQUENCE: 115
ggacaggggg cccaagtgat gctctggggt actggcgtgg gagagtggat ttccgaagct    60
gacagatggg tattctttga cgggggtag gggcggaacc tgaga                   105

<210> SEQ ID NO 116
<211> LENGTH: 105
<212> TYPE: DNA
<213> ORGANISM: Homo sapiens

<400> SEQUENCE: 116
ggaaagggac aggggccca agtgatgctc tggggtactg gcgtgggaga gtggatttcc    60
gaagctgaca gatgggtatt ctttgacggg gggtaggggc ggaac                  105

<210> SEQ ID NO 117
<211> LENGTH: 105
<212> TYPE: DNA
<213> ORGANISM: Homo sapiens

<400> SEQUENCE: 117
gaatgacact caagtgctgt ccatgaaaac tcaggaagtt tgcacaatta ctttctatga    60
cgtggtgata agacctttta gtctaggtta attttagttc tgtat                  105

<210> SEQ ID NO 118
<211> LENGTH: 105
<212> TYPE: DNA
<213> ORGANISM: Homo sapiens

<400> SEQUENCE: 118
ggggcggaac ctgagaggcg taaggcgttg tgaaccctgg ggagggggc agtttgtagg     60 tcgcgaggga agcgctgagg atcaggaagg gggcactgag tgtcc                  105

<210> SEQ ID NO 119
<211> LENGTH: 105
<212> TYPE: DNA
<213> ORGANISM: Homo sapiens

<400> SEQUENCE: 119
ggacaggggg cccaagtgat gctctggggt actggcgtgg gagagtggat ttccgaagct    60
gacagatggg tattctttga cgggggtag gggcggaacc tgaga                   105

<210> SEQ ID NO 120

```
<211> LENGTH: 105
<212> TYPE: DNA
<213> ORGANISM: Homo sapiens

<400> SEQUENCE: 120
ggacaggggg cccaagtgat gctctggggt actggcgtgg gagagtggat ttccgaagct    60
gacagatggg tattctttga cgggggtag gggcggaacc tgaga                    105

<210> SEQ ID NO 121
<211> LENGTH: 105
<212> TYPE: DNA
<213> ORGANISM: Homo sapiens

<400> SEQUENCE: 121
attaatttgg gattcctatg attatctcct atgcaaatga acagaattga ccttacatac    60
tagggaagaa aagacatgtc tagtaagatt aggctattgt aattg                    105

<210> SEQ ID NO 122
<211> LENGTH: 105
<212> TYPE: DNA
<213> ORGANISM: Homo sapiens

<400> SEQUENCE: 122
ggaaagggac aggggccca agtgatgctc tggggtactg gcgtgggaga gtggatttcc    60
gaagctgaca gatgggtatt ctttgacggg gggtagggc ggaac                    105

<210> SEQ ID NO 123
<211> LENGTH: 105
<212> TYPE: DNA
<213> ORGANISM: Homo sapiens

<400> SEQUENCE: 123
ggaaagggac aggggccca agtgatgctc tggggtactg gcgtgggaga gtggatttcc    60
gaagctgaca gatgggtatt ctttgacggg gggtagggc ggaac                    105

<210> SEQ ID NO 124
<211> LENGTH: 105
<212> TYPE: DNA
<213> ORGANISM: Homo sapiens

<400> SEQUENCE: 124
ggggcggaac ctgagaggcg taaggcgttg tgaaccctgg ggagggggc agtttgtagg    60 tcgcgaggga agcgctgagg atcaggaagg gggcactgag tgtcc                    105

<210> SEQ ID NO 125
<211> LENGTH: 105
<212> TYPE: DNA
<213> ORGANISM: Homo sapiens

<400> SEQUENCE: 125
cttaacaggc actgaaaaga gagtgggtag atacagtact gtaattagat tattctgaag    60
accatttggg acctttacaa cccacaaaat ctcttggcag agtta                    105

<210> SEQ ID NO 126
<211> LENGTH: 105
<212> TYPE: DNA
<213> ORGANISM: Homo sapiens

<400> SEQUENCE: 126
ggaaagggac aggggccca agtgatgctc tggggtactg gcgtgggaga gtggatttcc    60
```
gaagctgaca gatgggtatt ctttgacggg gggtaggggc ggaac    105

<210> SEQ ID NO 127
<211> LENGTH: 105
<212> TYPE: DNA
<213> ORGANISM: Homo sapiens

<400> SEQUENCE: 127
ggggcggaac ctgagaggcg taaggcgttg tgaaccctgg ggagggggc agtttgtagg    60 tcgcgaggga agcgctgagg atcaggaagg gggcactgag tgtcc    105

<210> SEQ ID NO 128
<211> LENGTH: 105
<212> TYPE: DNA
<213> ORGANISM: Homo sapiens

<400> SEQUENCE: 128
ggaaagggac aggggccca agtgatgctc tggggtactg gcgtgggaga gtggatttcc    60
gaagctgaca gatgggtatt ctttgacggg gggtaggggc ggaac    105

<210> SEQ ID NO 129
<211> LENGTH: 105
<212> TYPE: DNA
<213> ORGANISM: Homo sapiens

<400> SEQUENCE: 129
ggacaggggg cccaagtgat gctctggggt actggcgtgg gagagtggat ttccgaagct    60
gacagatggg tattctttga cgggggtag gggcggaacc tgaga    105

<210> SEQ ID NO 130
<211> LENGTH: 105
<212> TYPE: DNA
<213> ORGANISM: Homo sapiens

<400> SEQUENCE: 130
ggaaagggac aggggccca agtgatgctc tggggtactg gcgtgggaga gtggatttcc    60
gaagctgaca gatgggtatt ctttgacggg gggtaggggc ggaac    105

<210> SEQ ID NO 131
<211> LENGTH: 105
<212> TYPE: DNA
<213> ORGANISM: Homo sapiens

<400> SEQUENCE: 131
gaatgacact caagtgctgt ccatgaaaac tcaggaagtt tgcacaatta ctttctatga    60
cgtggtgata agacctttta gtctaggtta attttagttc tgtat    105

<210> SEQ ID NO 132
<211> LENGTH: 105
<212> TYPE: DNA
<213> ORGANISM: Homo sapiens

<400> SEQUENCE: 132
ggacaggggg cccaagtgat gctctggggt actggcgtgg gagagtggat ttccgaagct    60
gacagatggg tattctttga cgggggtag gggcggaacc tgaga    105

<210> SEQ ID NO 133
<211> LENGTH: 105
<212> TYPE: DNA

<213> ORGANISM: Homo sapiens

<400> SEQUENCE: 133
tgtttgcccc agtctatttu tagaagtgag ctaaatgttt atgcttttgg ggagcacatt     60
ttacaaattt ccaagtatag ttaaaggaac tgcttcttaa acttg                    105

<210> SEQ ID NO 134
<211> LENGTH: 105
<212> TYPE: DNA
<213> ORGANISM: Homo sapiens

<400> SEQUENCE: 134
ggacaggggg cccaagtgat gctctggggt actggcgtgg gagagtggat ttccgaagct    60
gacagatggg tattctttga cggggggtag gggcggaacc tgaga                    105

<210> SEQ ID NO 135
<211> LENGTH: 105
<212> TYPE: DNA
<213> ORGANISM: Homo sapiens

<400> SEQUENCE: 135
ggaaagggac aggggggccca agtgatgctc tggggtactg gcgtgggaga gtggatttcc   60
gaagctgaca gatgggtatt ctttgacggg gggtagggc ggaac                     105

<210> SEQ ID NO 136
<211> LENGTH: 105
<212> TYPE: DNA
<213> ORGANISM: Homo sapiens

<400> SEQUENCE: 136
ggacaggggg cccaagtgat gctctggggt actggcgtgg gagagtggat ttccgaagct    60
gacagatggg tattctttga cggggggtag gggcggaacc tgaga                    105

<210> SEQ ID NO 137
<211> LENGTH: 105
<212> TYPE: DNA
<213> ORGANISM: Homo sapiens

<400> SEQUENCE: 137
ggggcggaac ctgagaggcg taaggcgttg tgaaccctgg ggaggggggc agtttgtagg    60
tcgcgaggga agcgctgagg atcaggaagg gggcactgag tgtcc                    105

<210> SEQ ID NO 138
<211> LENGTH: 105
<212> TYPE: DNA
<213> ORGANISM: Homo sapiens

<400> SEQUENCE: 138
ggacaggggg cccaagtgat gctctggggt actggcgtgg gagagtggat ttccgaagct    60
gacagatggg tattctttga cggggggtag gggcggaacc tgaga                    105

<210> SEQ ID NO 139
<211> LENGTH: 105
<212> TYPE: DNA
<213> ORGANISM: Homo sapiens

<400> SEQUENCE: 139
ggacaggggg cccaagtgat gctctggggt actggcgtgg gagagtggat ttccgaagct    60
gacagatggg tattctttga cggggggtag gggcggaacc tgaga                    105

<210> SEQ ID NO 140
<211> LENGTH: 105
<212> TYPE: DNA
<213> ORGANISM: Homo sapiens

<400> SEQUENCE: 140
ggaaagggac aggggcccca agtgatgctc tggggtactg gcgtgggaga gtggatttcc    60
gaagctgaca gatgggtatt ctttgacggg gggtaggggc ggaac                  105

<210> SEQ ID NO 141
<211> LENGTH: 105
<212> TYPE: DNA
<213> ORGANISM: Homo sapiens

<400> SEQUENCE: 141
gaatgacact caagtgctgt ccatgaaaac tcaggaagtt tgcacaatta ctttctatga    60
cgtggtgata agacctttta gtctaggtta attttagttc tgtat                  105

<210> SEQ ID NO 142
<211> LENGTH: 105
<212> TYPE: DNA
<213> ORGANISM: Homo sapiens

<400> SEQUENCE: 142
ggaaagggac aggggcccca agtgatgctc tggggtactg gcgtgggaga gtggatttcc    60
gaagctgaca gatgggtatt ctttgacggg gggtaggggc ggaac                  105

<210> SEQ ID NO 143
<211> LENGTH: 105
<212> TYPE: DNA
<213> ORGANISM: Homo sapiens

<400> SEQUENCE: 143
ggacaggggg cccaagtgat gctctggggt actggcgtgg gagagtggat ttccgaagct    60
gacagatggg tattctttga cggggggtag gggcggaacc tgaga                  105

<210> SEQ ID NO 144
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
tttttttttt tttt                                                     14

<210> SEQ ID NO 145
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
tttttttttt tttt                                                     14

<210> SEQ ID NO 146
<211> LENGTH: 14
<212> TYPE: DNA

-continued

```
<213> ORGANISM: Artificial Sequence
<220> FEATURE:
<223> OTHER INFORMATION: Description of Artificial Sequence: Synthetic
      oligonucleotide

<400> SEQUENCE: 146
tttttttttt tttt                                                      14
```